(12) United States Patent
Viovy et al.

(10) Patent No.: US 10,767,151 B2
(45) Date of Patent: Sep. 8, 2020

(54) DEVICE FOR CELL CULTURE

(75) Inventors: Jean-Louis Viovy, Paris (FR);
Jean-Michel Peyrin, Paris (FR);
Bernard Brugg, Cergy (FR); Laure Saias, Paris (FR); Paul Gougis, Paris (FR); Maeva Vignes, Paris (FR)

(73) Assignees: CNRS-DAE, Paris (FR); INSTITUT CURIE, Paris (FR); SORBONNE UNIVERSITE, Paris (FR)

( * ) Notice: Subject to any disclaimer, the term of this patent is extended or adjusted under 35 U.S.C. 154(b) by 911 days.

(21) Appl. No.: 13/123,628

(22) PCT Filed: Oct. 12, 2009

(86) PCT No.: PCT/FR2009/001198
§ 371 (c)(1),
(2), (4) Date: Jul. 8, 2011

(87) PCT Pub. No.: WO2010/040920
PCT Pub. Date: Apr. 15, 2010

(65) Prior Publication Data
US 2011/0306041 A1    Dec. 15, 2011

(30) Foreign Application Priority Data
Oct. 10, 2008  (FR) ...................................... 08 05606

(51) Int. Cl.
*C12M 3/00*     (2006.01)
*C12N 5/0793*   (2010.01)
(Continued)

(52) U.S. Cl.
CPC ............ *C12M 29/10* (2013.01); *C12M 23/16* (2013.01); *C12M 23/34* (2013.01); *C12M 35/08* (2013.01); *C12N 5/0619* (2013.01)

(58) Field of Classification Search
CPC ....................................................... C12M 23/34
(Continued)

(56) References Cited

U.S. PATENT DOCUMENTS 5,866,345 A * 2/1999 Wilding ............... B01J 19/0093
366/DIG. 3
6,143,496 A * 11/2000 Brown et al. ................. 435/6.11
(Continued)

FOREIGN PATENT DOCUMENTS

EP        0 483 117 A2      4/1992
KR    100709284 B1 *       4/2007  ............ C12M 23/12
(Continued)

OTHER PUBLICATIONS

Peyrin et al. "Microfluidic chips with "Axon Diodes" for Directed Axonal Outgrowth and Re-construction of Complex Live Neural Network, (2008), 1329-1331".*
(Continued)

*Primary Examiner* — Liban M Hassan
(74) *Attorney, Agent, or Firm* — Oliff PLC

(57) ABSTRACT

A device for cell culture, in particular of neuronal cells, including: a substrate defining a first microfluidic chamber to be seeded with a first cell culture, and at least a second microfluidic chamber, a fluidic interconnection system connecting the first and second chambers and enabling cellular extensions, in particular axons, to extend from one chamber to the other, wherein the interconnection system of the device is made so as to promote the progression of at least one first type of cellular extension, the first and second types of extension being different either due to the microfluidic chamber from which they originate, or due to the type of cell of which they constitute an extension.

19 Claims, 17 Drawing Sheets

(51) Int. Cl.

| | |
|---|---|
| *C12Q 1/02* | (2006.01) |
| *C12Q 1/37* | (2006.01) |
| *C12Q 1/68* | (2018.01) |
| *G01N 33/566* | (2006.01) |
| *C12M 1/00* | (2006.01) |
| *C12M 3/06* | (2006.01) |
| *C12M 1/42* | (2006.01) |

(58) Field of Classification Search
USPC .................................................... 435/288.5
See application file for complete search history.

(56) References Cited

U.S. PATENT DOCUMENTS

| | | | | |
|---|---|---|---|---|
| 7,419,822 | B2* | 9/2008 | Jeon ...................... | B01F 5/0641 422/504 |
| 2003/0003571 | A1* | 1/2003 | Kanegasaki et al. ...... | 435/288.5 |
| 2006/0194273 | A1* | 8/2006 | Thomas .......................... | 435/29 |
| 2007/0243523 | A1* | 10/2007 | Ionescu-Zanetti .......................... | B01L 3/502738 435/4 |
| 2008/0132422 | A1* | 6/2008 | Bohlen .............. | G01N 33/5008 506/10 |
| 2009/0098541 | A1* | 4/2009 | Southern ........... | B01L 3/502753 435/6.11 |

FOREIGN PATENT DOCUMENTS

| | | | | |
|---|---|---|---|---|
| KR | 20080030297 A | * | 4/2008 | ............ C12M 23/12 |
| WO | WO 2004/029221 A2 | | 4/2004 | |
| WO | WO 2004/034016 A2 | | 4/2004 | |
| WO | WO 2006/037033 A2 | | 4/2006 | |

OTHER PUBLICATIONS

Kawak et al."English machine translation of KR100709284B1". (Year: 2007).*
Hong et al., "English language machine translation of KR-20080030297-A". (Year: 2008).*
Park et al., "Microfluidic culture platform for neuroscience research, vol. 1, 2128-2136" (Year: 2006).*
Sorensen et al., "Long-term neurite orientation on astrocyte monolayers aligned by microtopography, Biomaterials 28 (2007) 5498-5508." (Year: 2007).*
Liu et al., "A Microfluidic Chamber of Analysis of Neuron-to-cell Spread and Axonal Transport of an Alpha-Herpesvirus, vol. 3, 1-8." (Year: 2008).*
Taylor et al., "Microfluidic Multicompartment Device for Neuroscience Research," Langmuir, 2003, vol. 19, pp. 1551-1556.
Taylor et al., "A microfluidic culture platform for CNS axonal injury, regeneration and transport," Nature Methods, Aug. 2005, vol. 2, No. 8, pp. 599-605.
Gross et al., "Application of microfluidics for neuronal studies," Journal of the Neurological Sciences, vol. 252, 2007, pp. 135-143.
"Nano SU-8 Negative Tone Photoresist Formulations 2-25," Micro Chem, Feb. 2002.
Campenot, "Local control of neurite development by nerve growth factor," Proc. Natl. Acad. Sci. USA, vol. 74, No. 10, Oct. 1977, pp. 4516-4519.
Willaime et al., "Ceramide-induced apoptosis in cortical neurons is mediated by an increase in p38 phosphorylation and not by the decrease in ERK phosphorylation," European Journal of Neuroscience, vol. 13, 2001, pp. 2037-2046.
Whitesides et al., "Soft Lithography in Biology and Biochemistry," Annu. Rev. Biomed. Eng., vol. 3, 2001, pp. 335-373.
Fink et al., "Comparative study and improvement of current cell micro-patterning techniques," Lab Chip, 2007, vol. 7, pp. 672-680.
Nakanishi et al., "Photoactivation of a Substrate for Cell Adhesion under Standard Fluorescence Microscopes," J. Am. Chem. Soc. 2004, vol. 126, pp. 16314-16315.
Gallo et al., "Regulation of Growth Cone Actin Filaments by Guidance Cues," J. Neurobiol., vol. 58, 2004, pp. 92-102.
International Search Report issued in PCT/FR2009/001198, dated Aug. 18, 2010. (with English-language translation).
Written Opinion of the International Searching Authority issued in PCT/FR2009/001198, dated Aug. 18, 2010. (with English-language translation).
French Search Report issued in FR 0805606, dated Sep. 14, 2009. (with English-language translation).
French Written Opinion issued in FR 0805606, dated Sep. 14, 2009. (with English-language translation).
Kanagasabapathi et al., "In-Vitro Compartmented Neurofluidic System for Studying Neural Networks," Proceedings MEA Meeting 2008, Jul. 8-11, 2008, pp. 317-318.
Sep. 29, 2015 Third Party Observation issued in European Application No. 09752400.3.
Hoshino Takayuki et al. "Development of a regeneration-type neural interface: A cicrotube guide for axon growth of neuronal cells fabricated using focused-ion-beam chemical vapo deposition" J. Vac. Sci. Technol.; B 24(5); Nov./Dec. 2006; pp. 2538-2543.
Park Jeong Won et al. "Microfluidic culture platform for neuroscience research" Nature Protocols; vol. 1; No. 4; 2006; pp. 2128-2136.

* cited by examiner

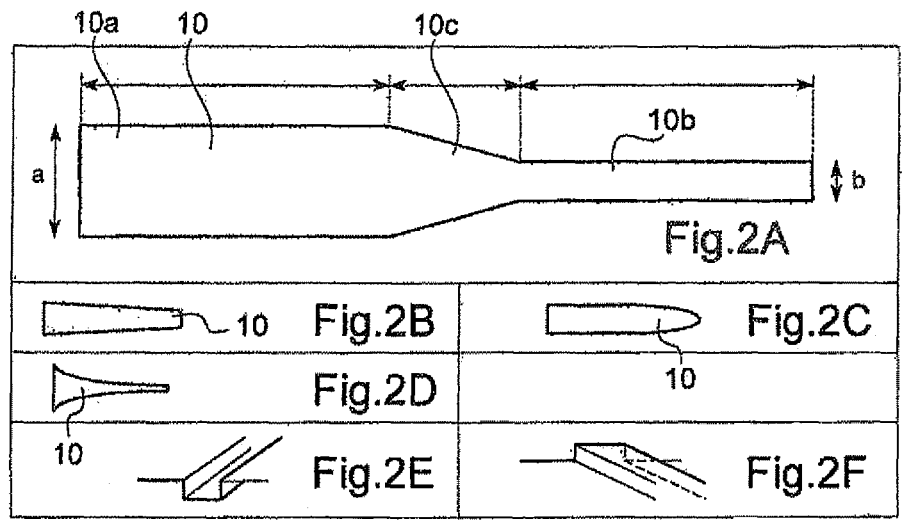
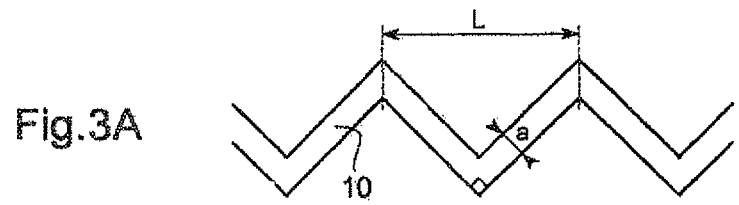
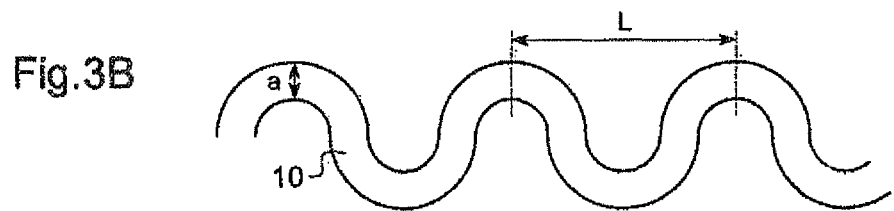
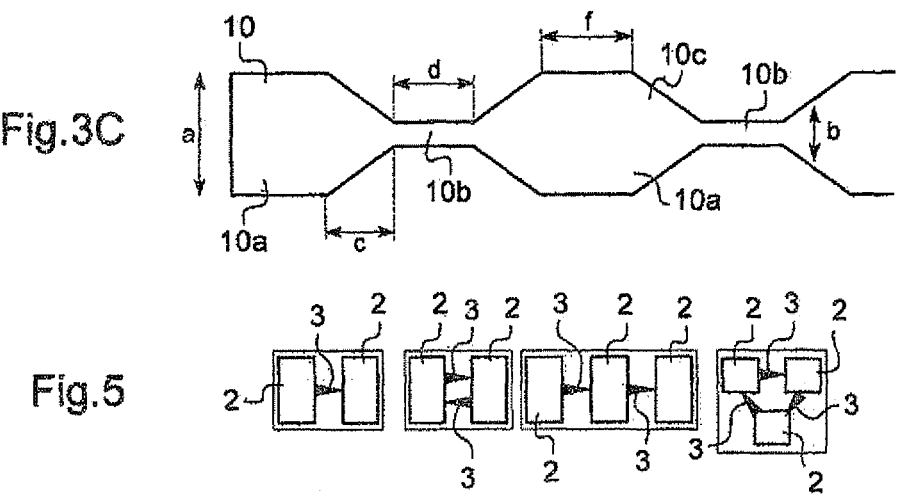

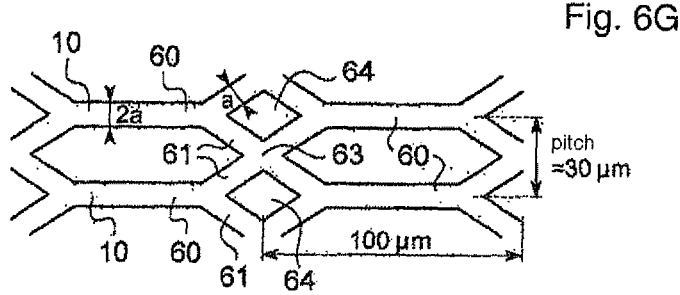
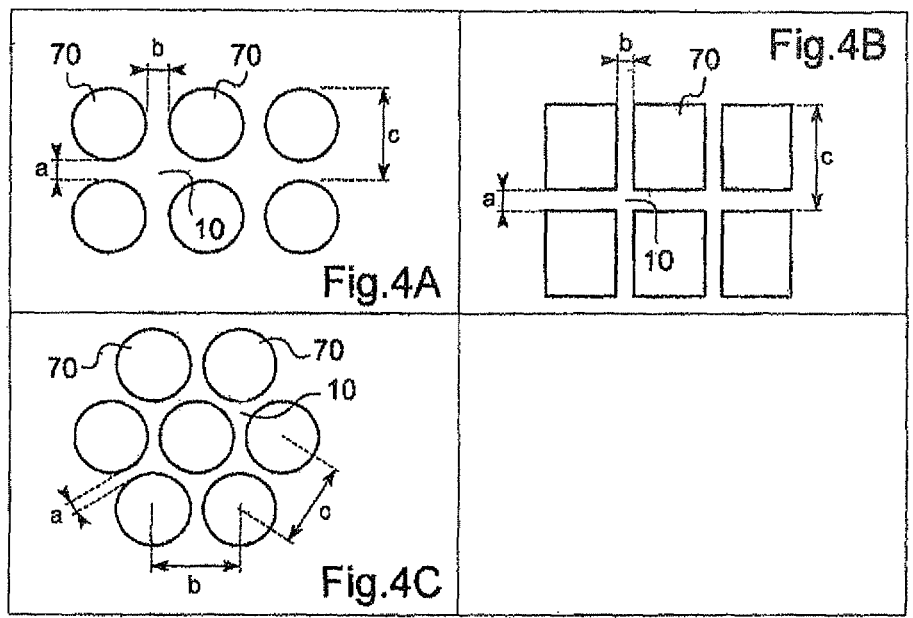
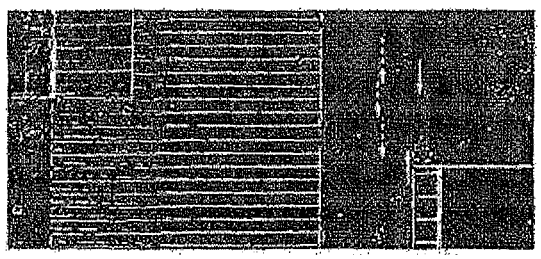
Fig. 11

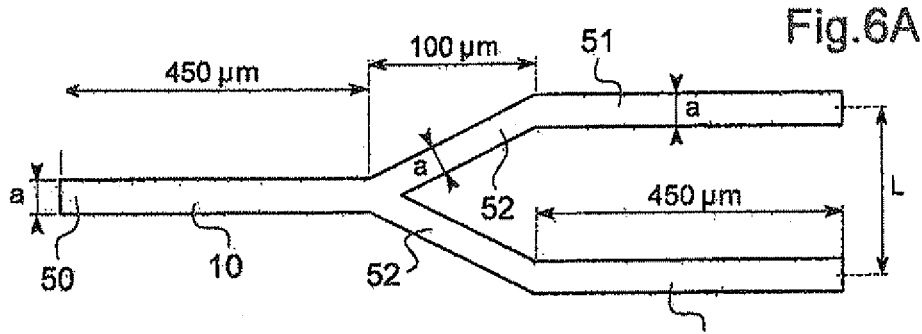
Fig.6A
| | A | B | C | D | E |
|---|---|---|---|---|---|
| a | 10 | 10 | 5 | 5 | 3 |
| L | 30 | 60 | 30 | 60 | 30 |
Fig.6B
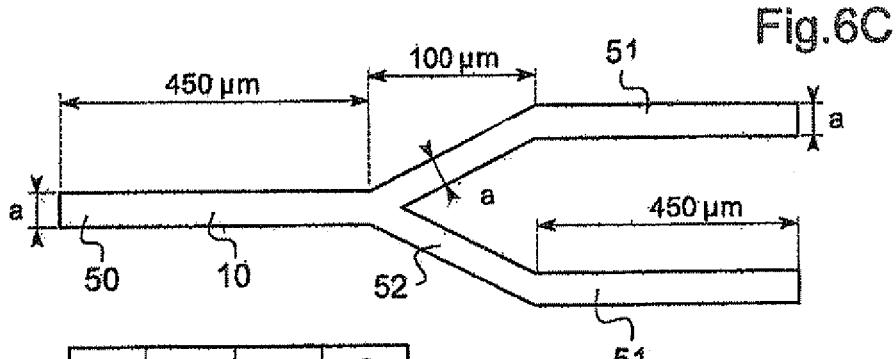
Fig.6C
| | A | B | C |
|---|---|---|---|
| a | 5 | 4 | 3 |
Fig.6D
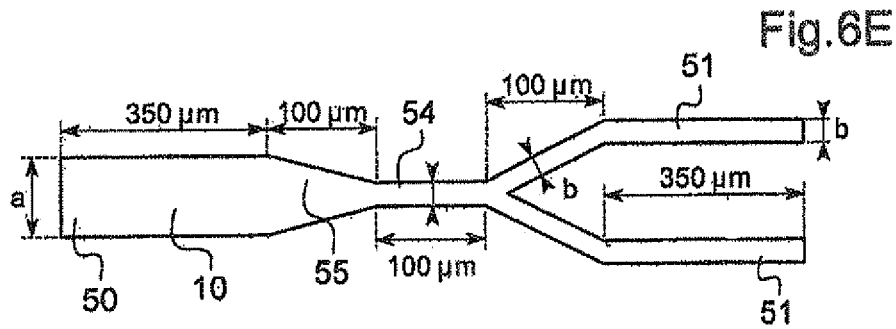
Fig.6E
| | A | B | C |
|---|---|---|---|
| a/b | 15/8 | 15/5 | 15/3 |
Fig.6F

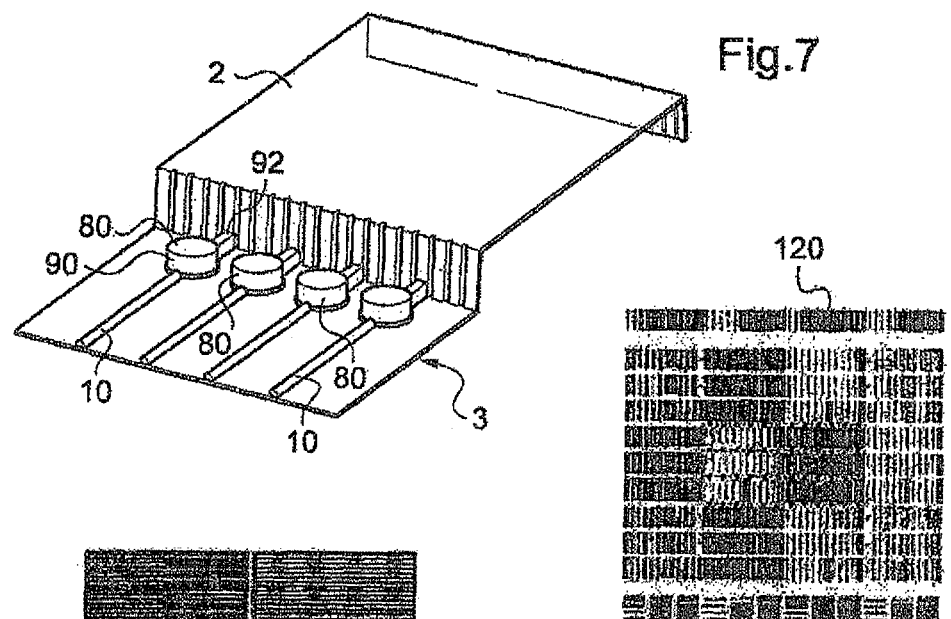
Fig.7
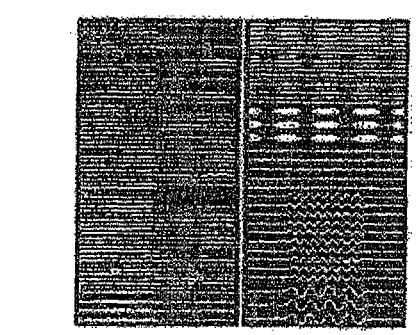
Fig.9
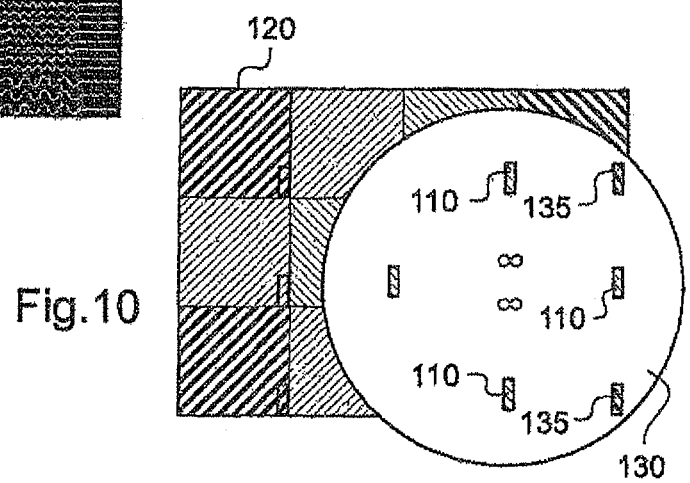
Fig.8
Fig.10
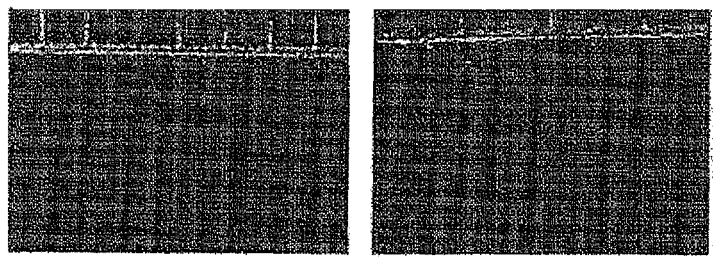
Fig.12

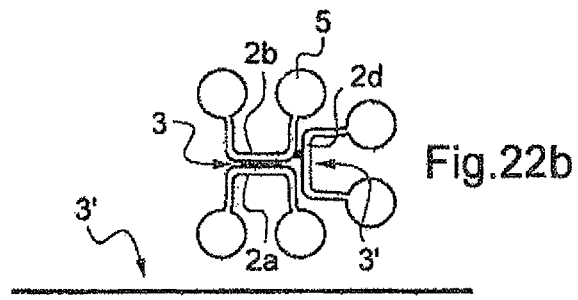
Fig.22b
Fig.23
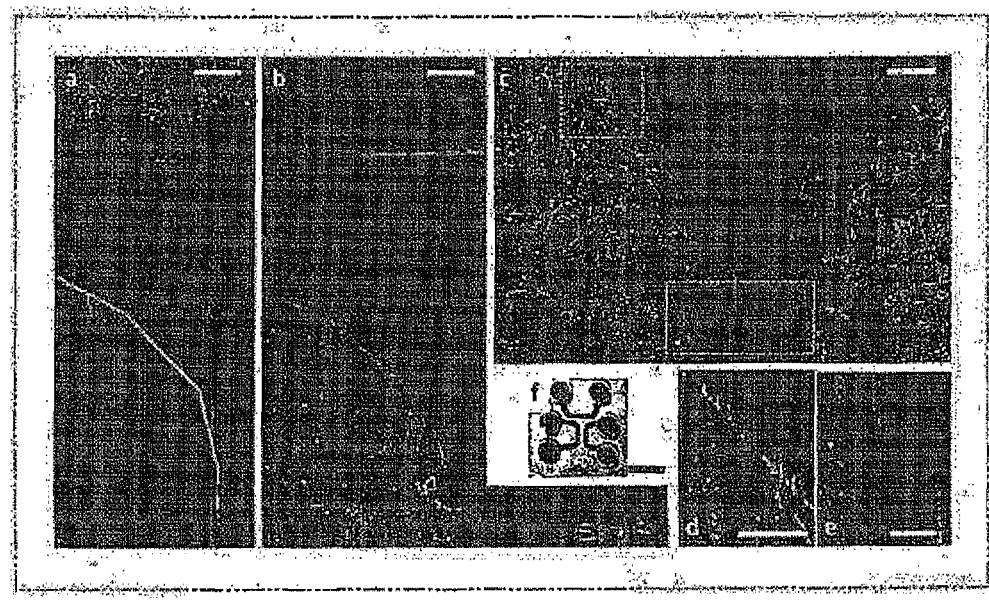
Fig.24
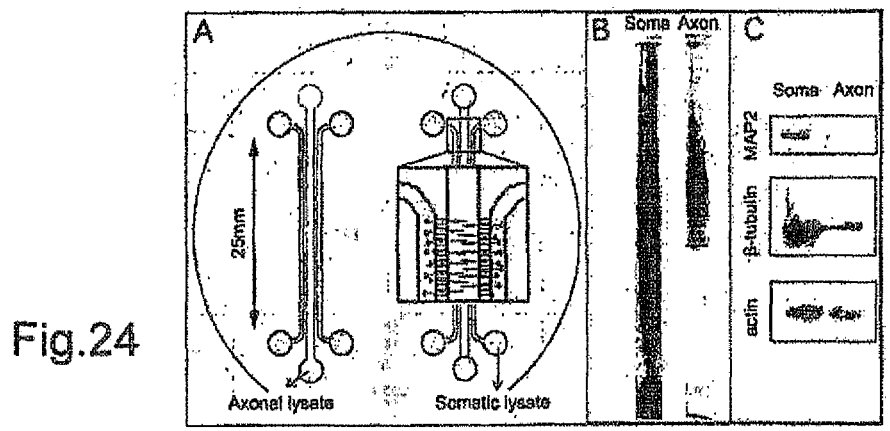

DEVICE FOR CELL CULTURE

CROSS-REFERENCE TO RELATED APPLICATIONS

Not applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

SEQUENCE LISTING

Not Applicable

BACKGROUND OF THE INVENTION

The present invention relates to devices and methods for cell culture, in particular of neuronal cells.

The brain is an extremely complex structure composed of several neuronal areas connected to one another. Experimental studies in vivo preserve this overall structure, but are not suitable for cell-scale study.

Cultures of disassociated cells make it possible to describe in much greater detail the system studied. For this reason, many laboratories perform neuronal cultures. Traditionally, these cultures of neurons are carried out in Petri dishes or culture wells. These cell cultures find applications as a reductionist model in the study of neurodegenerative diseases (Alzheimer's disease, Huntington's disease, Creutzfeldt-Jakob disease, etc.), but also in developmental biology for the understanding of molecular and cellular mechanisms of neuronal differentiation.

However, in these systems, the neuronal connections are made randomly and it is impossible to reconstitute therein an architecture similar to those that are found in vivo.

The network structure of the central nervous system (CNS) is completely absent, and does not make it possible to study how the various neuronal layers interact.

Another method consists in using slices of various parts of the brain, cultured ex vivo.

Even though the integrity of the neuronal layers is preserved by this method, the complexity of the tissues sampled quickly poses a problem. In order to understand more clearly the propagation of neuronal death and the mechanisms of development in the various layers of the brain, it is advisable to develop new experimental devices which make it possible to control the architecture of the networks of neurons cultured in vitro.

Microfluidics is a tool of choice for cell biology, and in particular for neurosciences.

In WO200434016, Jeon et al., inspired by the studies by Campenot [Campenot, R. B. Local control of neurite development by nerve growth factor, Proc. Natl. Acad. Sci. USA. 1977, 74(10), 4516-4519], propose a microfluidic circuit configuration which makes it possible to isolate the soma of neurons from their axon.

This configuration is suitable for the neurons of the central nervous system (CNS).

The "somatic" compartment is the channel into which the freshly dissected neurons are introduced.

The distal channel is that toward which the axons head in passing through the microchannels. The soma of the neurons cannot pass through the microchannels. This is because the microchannels are too thin to allow the soma to pass through.

This device is a first step toward the control of CNS neuronal cultures in vitro. The diffusion times in the microchannels are long, which makes it possible to treat the distal and somatic compartments separately. The diffusion of what is contained in one of the compartments toward the other is compensated for by imposing a pressure differential. For this, it is sufficient to place a larger volume of liquid in one of the reservoirs of one of the compartments, so as to impose a hydrostatic pressure differential between different compartments.

However, this device also has many limitations. Firstly, while it makes it possible to separate the cell compartments, it does not make it possible to induce any directed axonal connection between two neuron populations, since the axons can travel through the microchannels in both directions.

The publications WO 2006/037033 and U.S. Pat. No. 7,419,822, which are incorporated by way of reference, also relate to cell culture devices suitable for the culture of neurons.

The present invention aims, inter alia, to remedy these various limitations, and to thus allow studies, methods and screenings that are impossible with the current prior art devices.

SUMMARY

A subject of the invention, according to one of its aspects, is a device for cell culture, in particular of neuronal cells, comprising:
- a support defining a first microfluidic chamber intended to be seeded with a first cell culture, and at least a second microfluidic chamber,
- a fluidic interconnection system connecting the first and second microfluidic chambers and enabling cell extensions, in particular axons, to extend from one chamber to the other chamber, in which device the interconnection system is produced so as to promote the progression of at least one first type of cell extension compared with at least one second type of cell extension. Said first and second types of cell extension can differ due to the microfluidic chamber from which they originate and/or due to the cell type of which they are the extension.

The device can, in exemplary embodiments, make it possible to induce directed cell connections between two cell populations, in particular directed axonal connections.

The second microfluidic chamber can be seeded with at least one second cell type.

The interconnection system can comprise a plurality of channels, also called microchannels, and/or a plurality of microstructures.

The interconnection system can comprise at least one channel or one network of microstructures having an asymmetry between the side of said channel or of said network connected to the first microfluidic chamber, and the side of said channel or of said network connected to the second microfluidic chamber.

The interconnection system can comprise at least one channel of which at least one dimension becomes smaller as it progresses from one chamber to the other, said at least one dimension comprising, for example, the width of the channel. In particular, the interconnection system can comprise at least one narrowing channel, also called "diode". Said dimension can be less than or equal to 5 µm at the site where said channel opens into the first microfluidic chamber or into the second microfluidic chamber.

The interconnection system can comprise a channel of which at least one portion has a trapezoidal shape when observed from above. The channel can have a convergent portion extended by a portion of constant width.

The interconnection system can comprise a nonrectilinear channel. As a variant, all the channels of the interconnection system are rectilinear.

The interconnection system can comprise a channel comprising a succession of narrowings and widenings when progressing from one of the chambers to the other.

Said channels can have interconnections or branches.

The network of microstructures can comprise obstacles preventing the propagation of axons in a straight line.

The obstacles can be arranged so as to impose, on any continuous path between the first microfluidic chamber and the second microfluidic chamber, at least one portion in which the radius of curvature of said path is less than 20 µm, preferably less than 10 µm, even more preferably less than 7 µm, 5 µm, or even 3 µm.

The first chamber can be symmetrical with the other chamber relative to a plane of symmetry.

The distance between the first and the second chamber is, for example, between 3 µm and 10 000 µm, for example between 10 µm and 10 000 µm.

The interconnection system can comprise at least one portion of which the surface has been chemically or biochemically treated so as to have an affinity for at least one type of cell or one type of cell behavior.

The chemical treatment can comprise exposure to at least one type of molecule selected from fibronectin, cadherins, collagen, laminin, molecules comprising succinimide groups, N-sulfosuccinimidyl 6-[(4'-azido-2'-nitrophenyl)amino]hexanoate, and photoactivatable reactive chemical molecules.

The interconnection system can comprise microchannels or microstructures having a thickness that is less than that of the first and second microfluidic chambers, and preferably between 1 and 5 µm, even more preferably between 2 and 4 µm.

In exemplary embodiments, the only fluidic communication between the first or second chamber and the exterior of this chamber takes place by means of the interconnection system. As a variant, a fluidic communication can take place not only by means of the interconnection system, but also by means of at least one membrane which allows only solutes to pass through, and not cell extensions.

This membrane is, for example, located on the top of the chamber. It can, for example, be a microperforated PDMS or nitrocellulose membrane.

In exemplary embodiments of the invention, the interconnection system does not serve to filter a flow, in particular a blood flow.

The device can comprise at least one single-cell microfluidic chamber, proportioned so as to contain only the soma of a single cell, this single-cell microfluidic chamber communicating with the interconnection system and with one of the first and second microfluidic chambers.

The single-cell microfluidic chamber can have a thickness which is smaller than that of the first and second microfluidic chambers and larger than that of said interconnection system. The single-cell microfluidic chamber can be closer to one of the chambers than the other.

In exemplary embodiments of the invention, the microfluidic device comprises at least three microfluidic chambers, namely a first and a second chamber connected via a first interconnection system. At least one of the first and second systems is as defined above, namely enables cell extensions, in particular axons, to extend from one chamber to the other chamber, promoting the progression of at least one first type of cell extension compared with at least one second type of cell extension. Each interconnection system can comprise sets of microchannels. The microchannels of the second interconnection system can be oriented differently than in the extension of the microchannels of the first interconnection system, for example substantially perpendicular thereto. One of the advantages of this implementation is to reduce the risk of extensions which originate from the first chamber and reach the second chamber progressing to the third chamber.

The device can comprise at least one microfluidic chamber of which the volume is between 100 and 10 000 µm$^3$, and preferably between 500 and 5000 µm$^3$, and which communicates in a fluidic manner with the interconnection system and with one of the first and second microfluidic chambers.

Passing through the interconnection system can be at least one channel connecting, for example, two opposite regions, arranged on either side of the interconnection system. Such a channel can make it possible, for example, to reduce the risk of contamination of one chamber with a compound introduced into the other chamber. The channel can also make it possible to carry out an axotomy, by circulating therein a substance such as a detergent, for instance triton X or saponin. Any other molecule that can damage, protect or modify axon metabolism can be circulated in the channel.

The interconnection system can be delimited on at least one part of its surface by a porous wall enabling the exchange of molecules and ions with a secondary compartment, but not enabling the exchange, with said secondary compartment, of cells.

The device for cell culture can also comprise at least one microelectrode, and preferably a network of microelectrodes, connected to a measuring instrument for studying electrophysiological processes in at least one cell present in said device.

A subject of the invention, according to another of its aspects, is also a device for cell culture, comprising:
  first and second macrochannels,
  a microchannel connected at a first end to the first macrochannel,
  a single-cell microfluidic chamber communicating with the second macrochannel and with a second end of the microchannel, the first and second macrochannels communicating with one another by means of the microchannel and of the single-cell microfluidic chamber, the single-cell microfluidic chamber being proportioned so as to be able to receive only the soma of a single cell.

A subject of the invention, according to another of its aspects, is also a device for cell culture, comprising at least two interconnection systems, at least one of which, and preferably at least two of which, are produced as defined above.

A subject of the invention, according to another of its aspects, is also a device for cell culture, comprising at least three microfluidic chambers connected in series by at least two interconnection systems, in which the thickness of said interconnection systems is less than the thickness of said three microfluidic chambers, and at least one of said microfluidic chambers has a thickness between the thickness of at least one of the other microfluidic chambers and that of said interconnection systems.

A subject of the invention, according to another of its aspects, is also a device for cell culture, comprising at least three microfluidic chambers connected in series by at least two interconnection systems of different orientations, in particular, perpendicular orientations.

A subject of the invention, according to another of its aspects, is also a method for cell culture, in particular of neuronal cells, in which at least one microfluidic chamber of a device as defined above is seeded with neuronal cells.

It is possible to seed at at least two microfluidic chambers with neuronal cells, and the axons of the cells of one of the chambers find less difficulty in developing toward the other chamber than those of the cells of the other chamber owing to the form of the interconnection system.

It is possible to seed at least one microfluidic chamber with a cell culture having at least two cell types, and the axons of the cells of at least one of said cell types find less difficulty in developing in the interconnection system than the axons of the cells of at least one second cell type.

An axotomy can be carried out by means of a channel which passes through the interconnection system, as indicated above. The cells contained in one of the chambers can be brought into the presence of a compound. The above-mentioned channel can be filled with a liquid constituting an obstacle with respect to the progression of the compound toward the other chamber by means of the interconnection system.

A subject of the invention, according to another of its aspects, is also a method for studying biomarkers present in a cell compartment, comprising at least the steps of:
  culturing cells according to one of the methods defined above,
  bringing at least one of said cell compartments of at least one of said cells into the presence of probes for said biomarker,
  revealing and/or quantifying the presence of said biomarker by means of said probes.

A subject of the invention, according to another of its aspects, is also a method for studying the biomarkers present in a cell compartment, comprising at least the steps of:
  culturing cells according to one of the methods defined above,
  collecting the supernatant present in at least one of the microfluidic chambers, and investigating or quantifying one or more biomarkers in its content.

The investigating or quantifying of said biomarker(s) can involve at least the determination of the content in terms of a nucleotide sequence, or the determination of the content in terms of a polypeptide, or the determination of the content in terms of a metabolite, of said cell compartment or of said supernatant.

A subject of the invention, according to another of its aspects, is also a method for determining the reaction of certain cells to an entity, comprising the steps consisting in:
  a) culturing cells using one of the devices defined above, or one of the methods defined above, then
  b) bringing at least one of the cell compartments of said cells into the presence of said entity in at least one of the microfluidic chambers of said device.

This method can also comprise a step c) consisting in studying the effect of the stimulation carried out in step b) on another cell compartment or in another microfluidic chamber of the device.

The presence of a channel of liquid passing through the interconnection system can reduce the risk of migration of said entity toward the other chamber.

The method can be applied in parallel on several devices present on the same microfluidic support, involving, between at least two different devices, differences between at least one cell type, one type of buffer, one type of entity, or one type of interconnection system, in order to carry out a differential screening.

A subject of the invention, according to another of its aspects, is also a method for screening for neurotoxic agents, or for screening for neuroprotective medicaments, involving at least one device as defined above or one of the methods above.

BRIEF DESCRIPTION OF THE SEVERAL VIEWS OF THE DRAWINGS

FIGS. 2A to 2D represent microchannels of different shapes.

FIG. 3A is a microchannel in the shape of a zigzag with consecutive portions arranged at right angles to one another.

FIG. 38 is a microchannel 10 having an undulating shape composed of a succession of semicircular portions.

FIG. 3C represents a microchannel 10 comprising a succession of widened portions and narrowed portions.

FIGS. 4A to 4C give examples of interconnection systems of the type consisting of networks of obstacles.

FIG. 5 represents nonexhaustive examples of arrangements that can be used to form, by means of the invention, complex and oriented neuronal architectures;

FIG. 6A is an example of a microchannel with a bifurcation that comprises a first portion that joins up with two branches; FIG. 6B is a table of values for the parameters a and L for various examples of configurations A to E.

FIG. 6C represents a microchannel produced with a portion having a width 2a double that of the branches; FIG. 6D is a table of some examples of values for the width a, in various configurations A to C.

FIG. 6E represents a microchannel comprising a portion that narrows before splitting into two branches; FIG. 6F is a table of various examples of the a/b ratio for various configurations A to C.

FIG. 6G represents a configuration having properties similar to those of FIG. 6C with regard to the mechanical stresses on the Y-shaped zone. FIG. 6H is a table of examples a values for parameter a for various configurations A to C.

FIG. 7 represents an embodiment having single-cell chambers between the chambers.

FIG. 8 represents a quartz mask etched with a multiplicity of patterns of microchannels and cell chambers.

FIG. 9 represents two examples of patterns that can appear through a window of an overmask.

FIG. 10 represents an overmask having windows to a high-resolution mask.

FIG. 11 is a photograph of an exemplary embodiment of an interconnection system comprising microchannels of which the width decreases from one microfluidic chamber to the other.

FIG. 12 shows, on the left-hand photograph, the outlet of the narrowest microchannels, in 40× phase contrast, with a cortical culture alone, and, on the left-hand photograph, in the case of a coculture.

Figure 14:
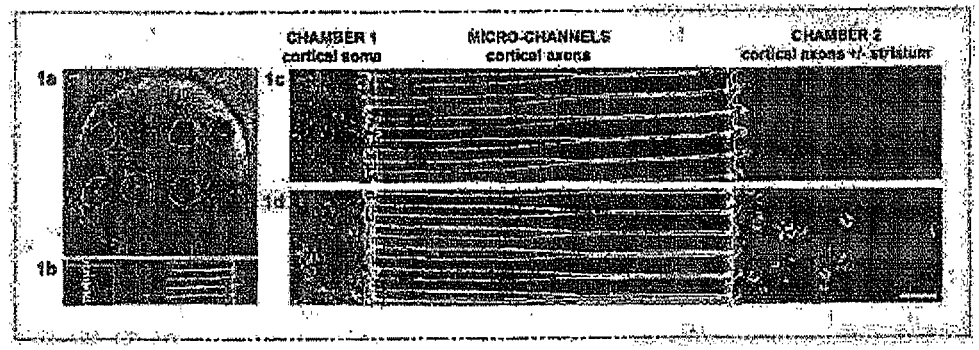

Photograph 1a of FIG. 14 represents microfluidic devices for neuron culture according to the invention, comprising two individual culture fields interconnected via a series of asymmetrical microchannels, some of which are visible on photograph 1b. Photographs c and d are images by phase contrast combined with epifluorescence of a polarized reconstructed neuronal network.

Figure 15:
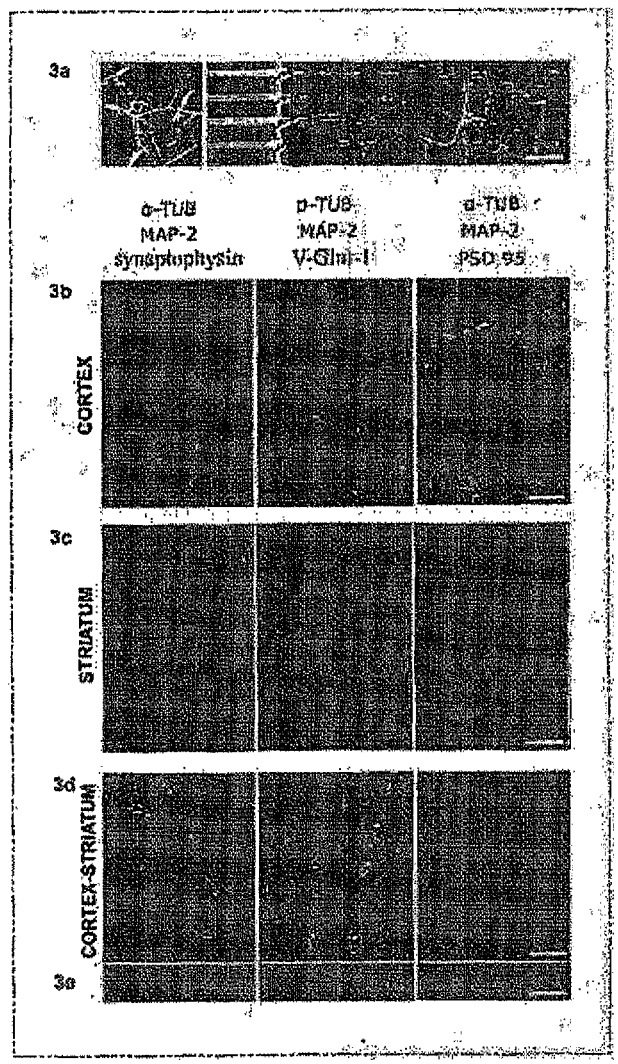

FIG. 15 are photographs of striatal neurons, after culturing for three days in the second chamber of a device according to the invention, and cortical neurons seeded in the first chamber.

Figure 16:
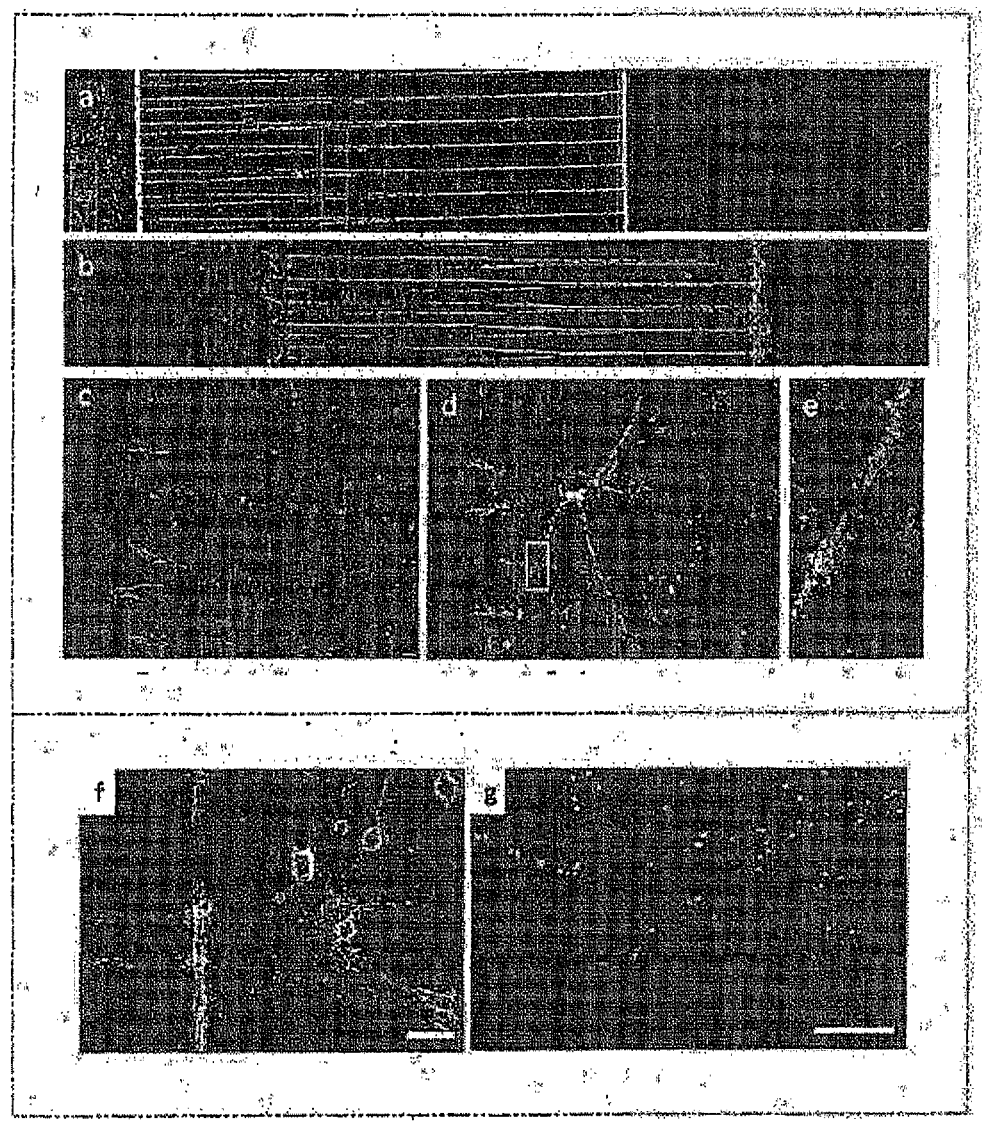

Photograph a, in phase contrast, of FIG. 16 represents a device seeded with cortices alone, and photograph b, in phase contrast also, represents a device seeded with cortices in the left-hand chamber, extending onto hippocampal neurons. Photographs c, d, and e correspond to immunofluorescent labelings. Photograph f represents a cortex-dentate gyrus network, with a bundle of cortical fibers contacting dentate gyrus neurons. Image g is similar, with labeling of the formation of cortico-hippocampal synapses along dendrites of dentate gyrus neurons.

Figure 17:
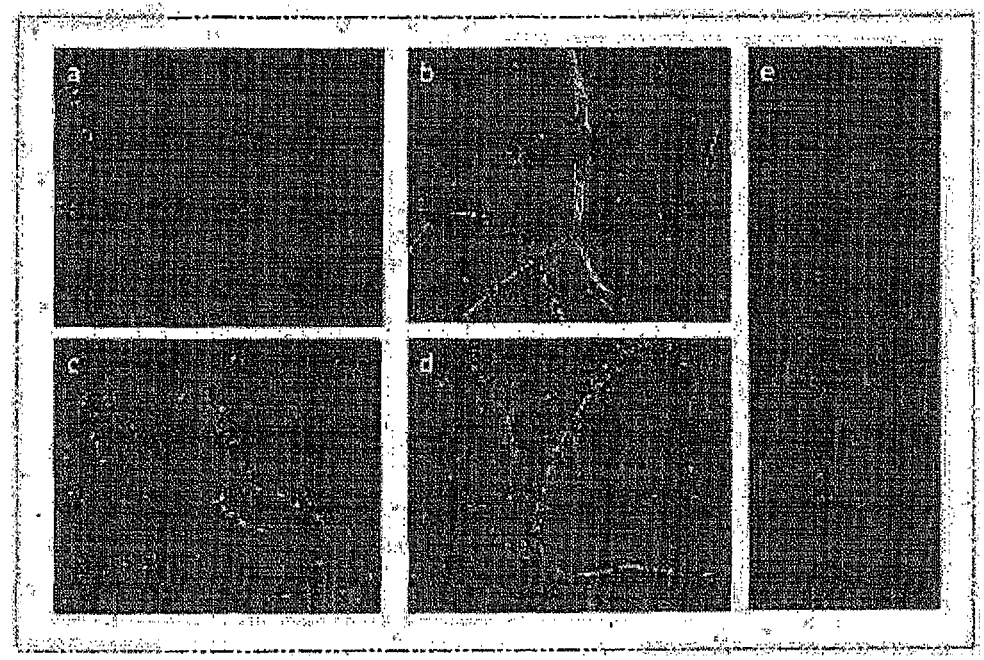

Photograph a of FIG. 17 corresponds to synaptophysin and axonal tubulin labeling of cortical neurons seeded alone. Photograph b is a photograph of hippocampal neurons seeded alone, without cortical afference. Photographs c and d are of bundles of cortical fibers and synaptophysin of the hippocampus. Photograph e is a magnification of a hippocampal dendrite.

Figure 18:
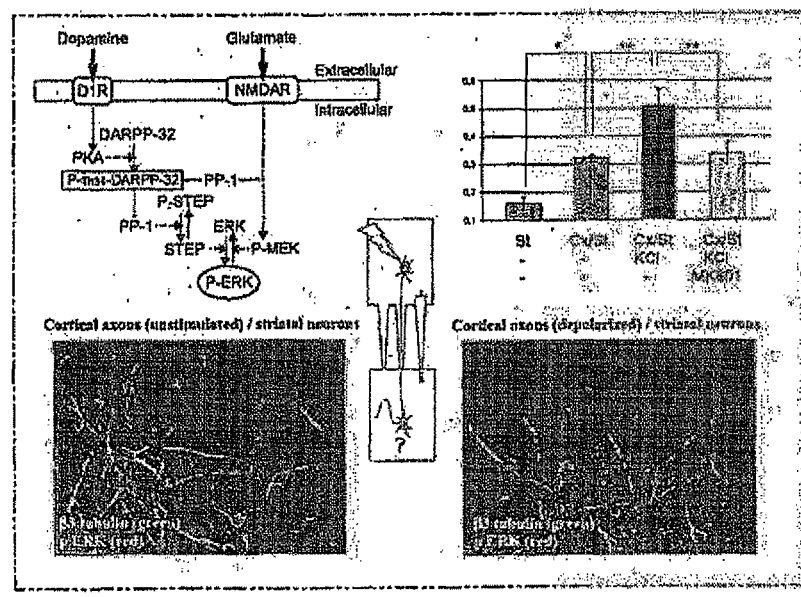

FIG. 18 represents microfluidic chambers separated by asymmetrical microchannels.

Figure 19:
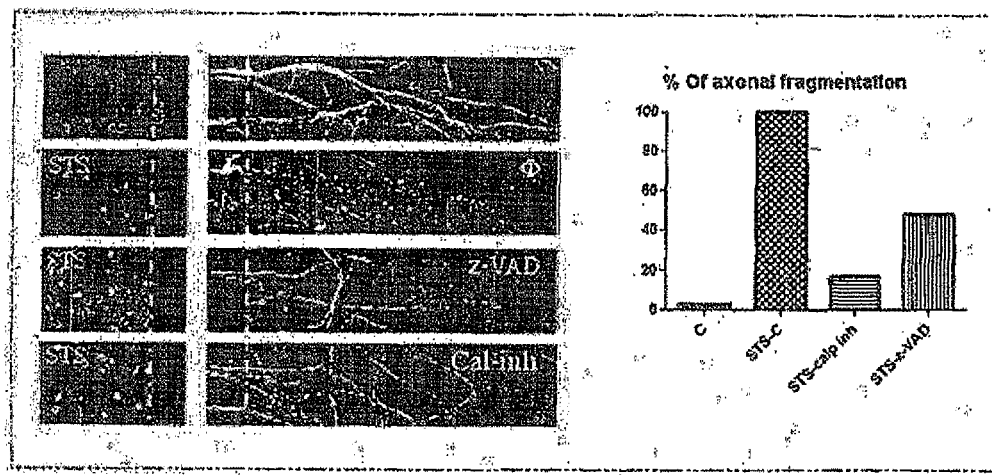

FIG. 19 represents photographs and a graph relating to Example 14.

Figure 20:
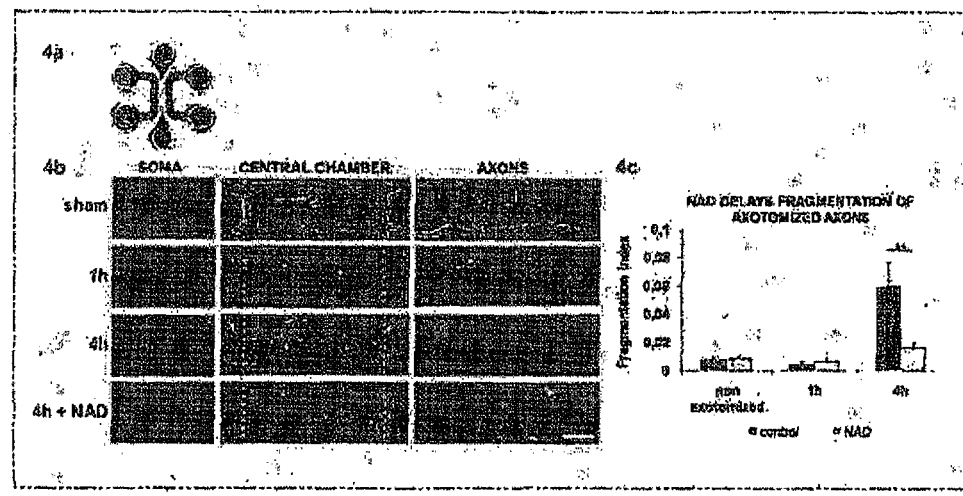

FIG. 20 contains a schematic of a microfluidic device, photographs, and a graph pertaining to Example 15.

Figure 21:
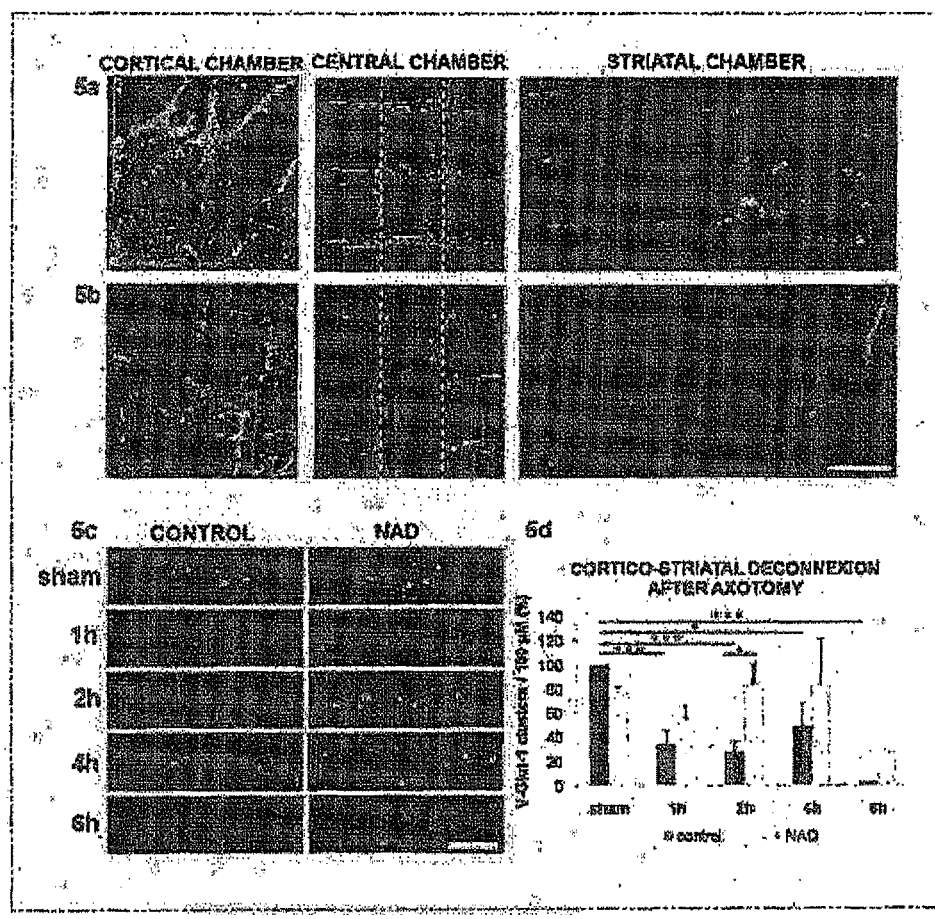

FIG. 21 represents photographs and a graph relating to Example 16.

Figure 22:
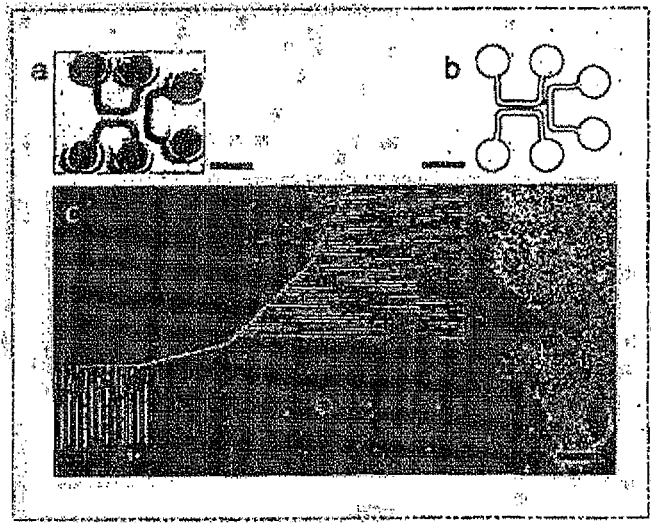

FIGS. 22, 22b and 23 contain schematical representations of a microfluidic device and photographs pertaining to Example 18.

FIG. 24 contains a schematic of a microfluidic device and photographs pertaining to Example 19.

Figure 25:
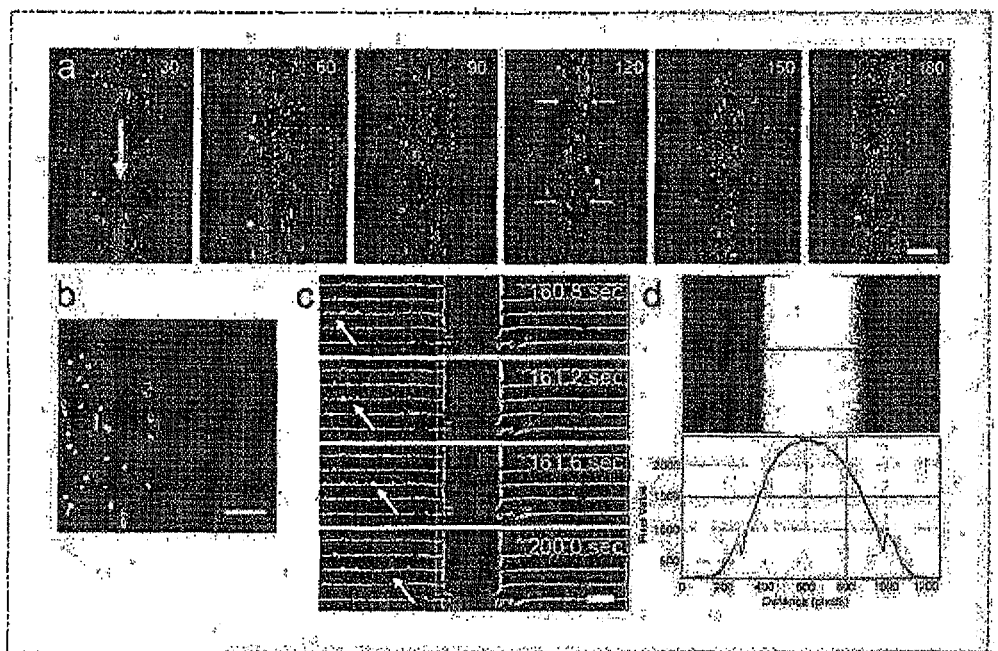

FIG. 25 represents photographs and a graph relating to Example 19.

Figure 26:
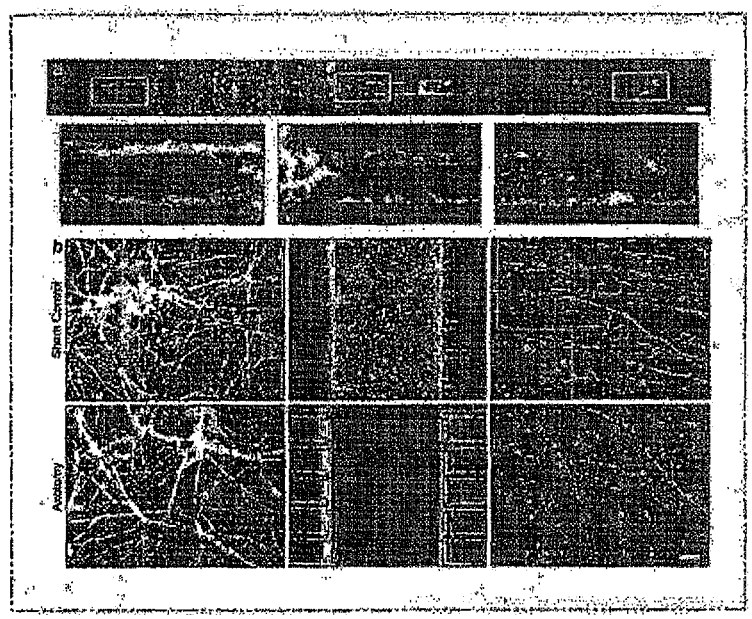

FIG. 26 contains photographs relating to Example 20.

Figure 27:
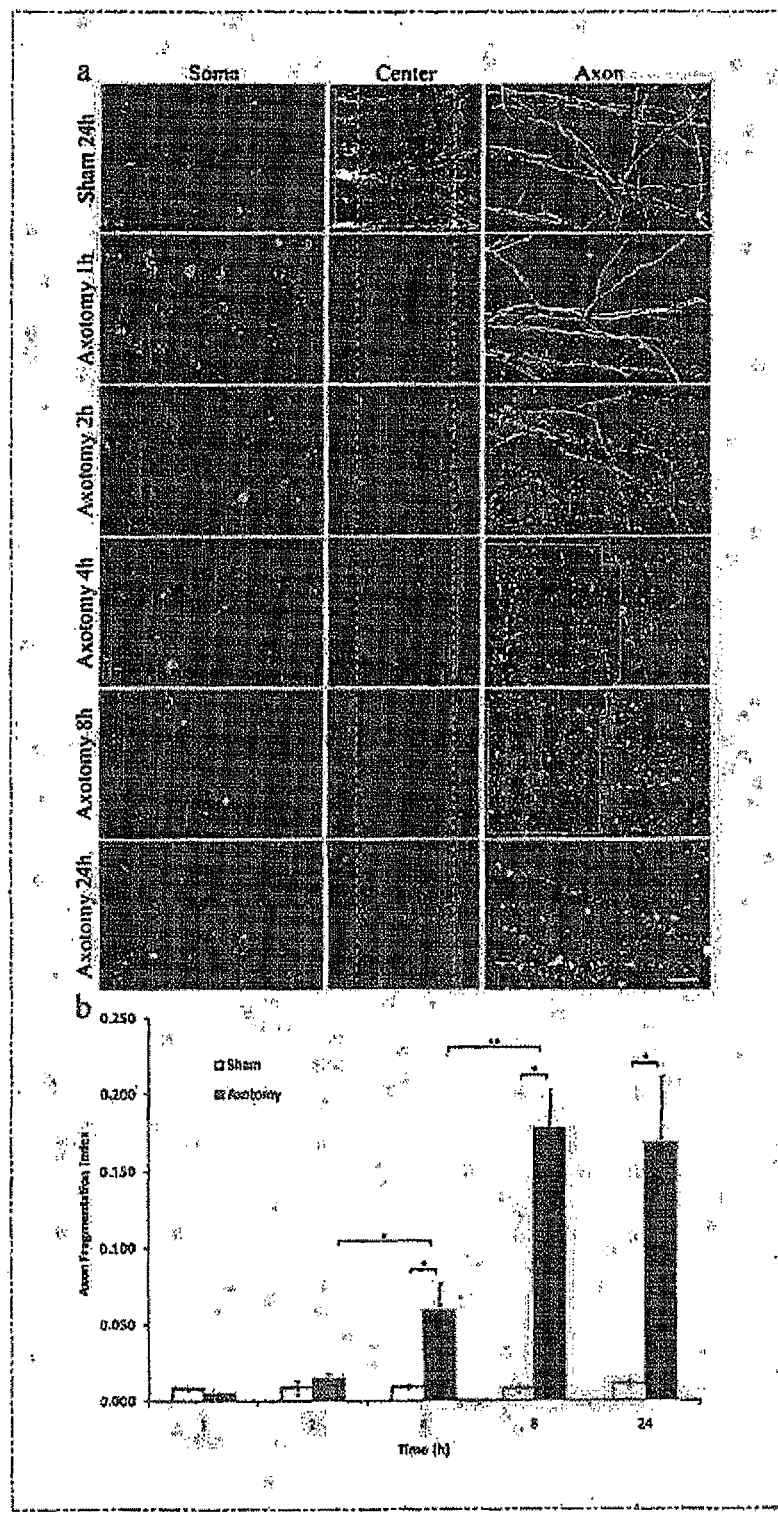
Figure 28:
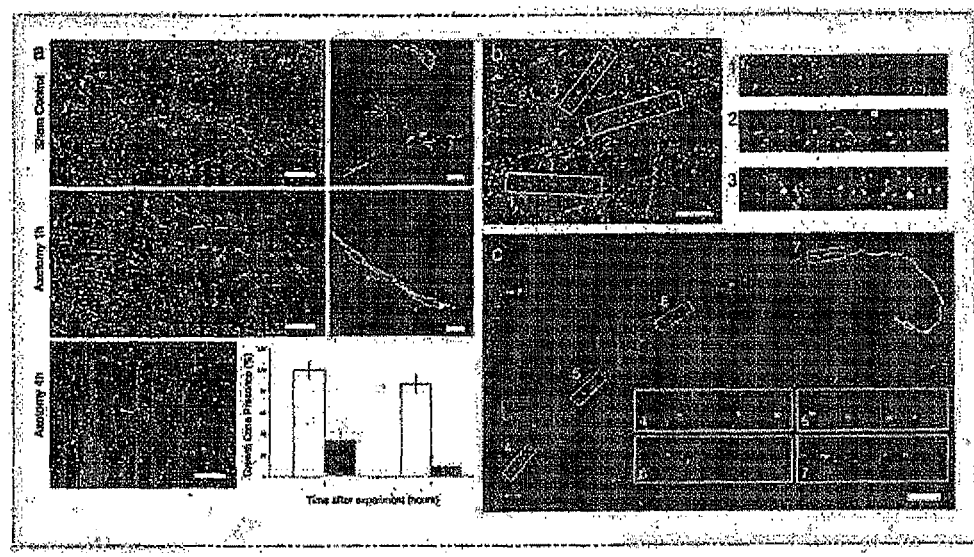

FIGS. 27 and 28 contain photographs and graphs relating to Example 20.

Figure 29:
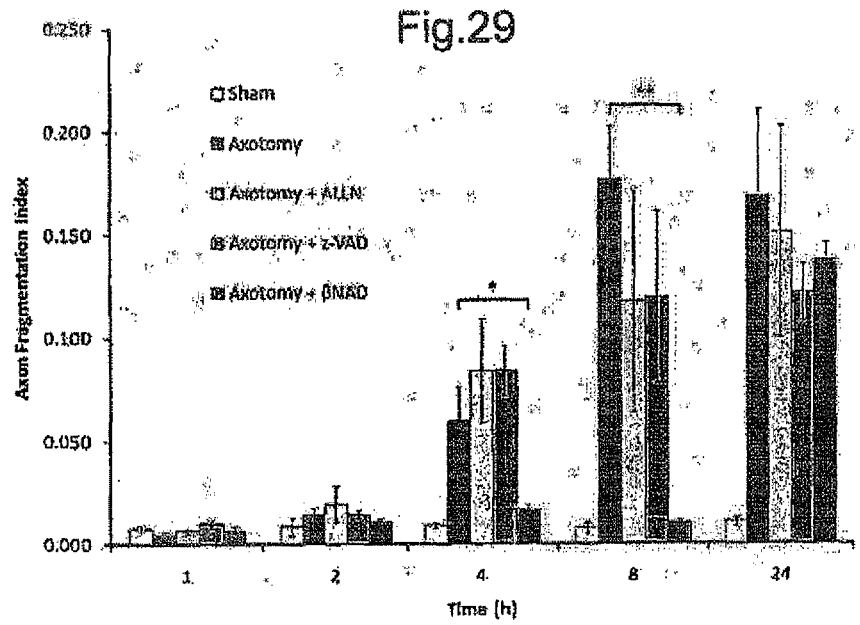

FIG. 29 is a graph related to Example 20.

Figure 30:
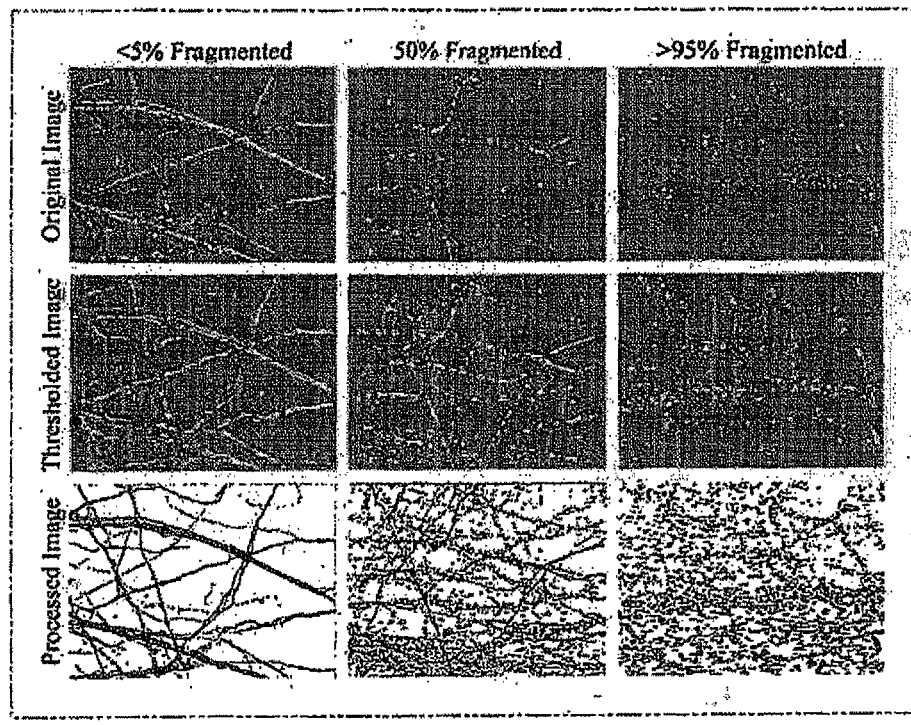

FIG. 30 shows the relationship between the fragmentation index and the % of fragmented axons, 0.005, 0.083 and 0.157 corresponding, respectively, to <5%, 50% and >95% of fragmented axons.

Figure 31:
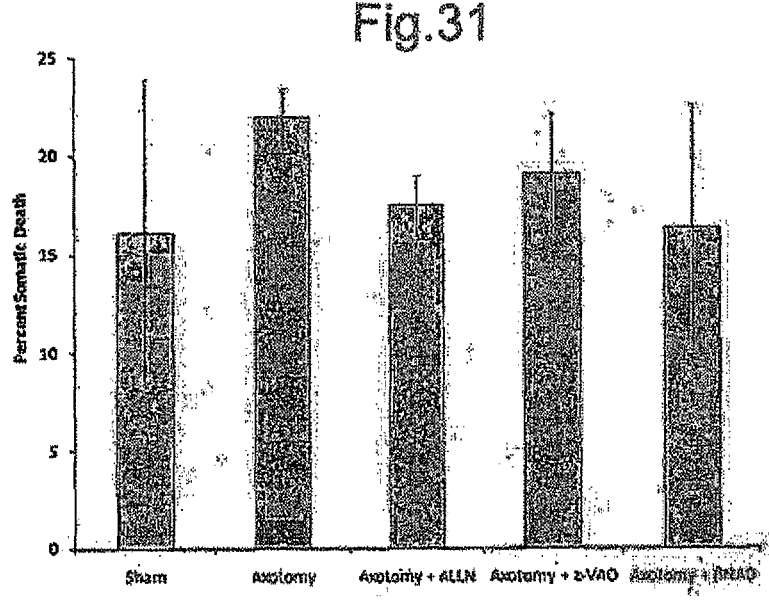

FIG. 31 is a graph depicting the proportion of somatic deaths, obtained by dividing the number of cell bodies showing labeling with Hoechst dye by the total number of bodies.

DETAILED DESCRIPTION OF THE INVENTION

The degeneration of neurons during neurological or neurodegenerative diseases proceeds by means of a succession of steps comprising an early modification of synaptic functionality (transmission), degeneration or retraction of the pre-synaptic elements, modifications of the parameters of retrograde and anterograde axonal transport, axonal destruction and degeneration of the somatodendritic compartment. The chronology of these events can depend on the type of attack undergone by the neuron (modification of neurotransmission upstream of the neuron, neurotoxic stress, gene mutation, viral infection, etc.). The cellular and molecular mechanisms associated with the dysfunction of these various compartments may be specific and nonredundant. It is important to note that the cellular or molecular mechanisms which control the integrity of the axon or of the synapses are not known and that they are probably not identical to those controlling the integrity of neuronal somas (and for which many pharmacological agents have been developed). Thus, a molecule known to protect the cell soma will not necessarily prevent synaptic or axonal degeneration (and vice-versa). Moreover, when neurons are connected to one another, the loss of afferent (upstream) connections can result in the neuron becoming fragile and then becoming more vulnerable to a neurotoxic stress. This can result in cascade degenerations in neuronal networks. The evaluation of molecules for therapeutic purposes on networks that have been reconstituted by means of a device according to the invention therefore makes it possible to evaluate their potential on the robustness of the networks. Axonal and synaptic disorders and probably network dysfunctions appear very early during neurodegenerative pathological conditions and appear to be correlated with the appearance of cognitive symptoms in patients.

A device according to the invention can make it possible to compartmentalize isolated neurons or to reconstruct oriented networks of neurons. The architectures of the devices make it possible to selectively apply fluids of varied composition, specifically on each of the subcompartments of the neuronal networks (for example, if a neuron of type A connected to a neuron of type B is considered, somatodendritic compartment of neuron A, portion of axon of neuron A, somatodendritic compartment of neuron B, axon of neuron B, etc.).

It is thus possible to model degenerative conditions by applying a stress to any part of the network, and to follow the consequences thereof. This stress can comprise, for example, axotomy of the axons of the neuron A, the application of toxic molecules to the somatodendritic or median axonal compartment of the neuron A, to the somatodendritic compartment of the neuron B, etc. The stress can comprise the application of toxic (of organic or inorganic nature), neurotoxic, synaptotoxic, axonotoxic, etc., molecules, of normal or mutated or chimeric proteins added to the cell medium or transferred genetically, of neurotropic (or non-neurotropic) viruses or infectious agents, of modifications of the physiochemical conditions, or physical conditions (pressure, temperature, waves, etc.).

The application of these stresses may cause a progressive degeneration of all or part of the cell components (modification of synaptic transmission, synaptic retraction, axonal degeneration, modification of axonal transport parameters, somatodendritic degeneration, etc.), the consequences of which may be followed by the analysis of biomarkers or of cell morphology.

The occurrence of these degenerative processes may be blocked or curbed by applying, locally to a component of the network, molecules of which it is desired to evaluate the pharmacological properties (organic molecules resulting from chemical synthesis or natural extraction, proteins (neurotrophic factors, etc.), natural or unnatural polymers). Their properties may be evaluated with respect to the ability to restore i) synaptic functionality (for example illustrated in FIG. 18 by the experiments of mobilization, in striatal neurons, of the erk kinase, after cortical stimulation), ii) synaptic degeneration (for example illustrated in FIG. 21 by the experiments of monitoring the VGlut-1 presynaptic structures in the axotomy experiments), iii) axonal degeneration or somatic degeneration (for example illustrated in FIGS. 19 and 20 by the experiments of cortical neuron axotomy and somatic staurosporin application). Similarly, it is possible to evaluate the potential of molecules aimed at regenerating the structures destroyed (neurotrophic factors, etc.).

A device according to the invention can be most particularly suitable for studying axonal or synaptic degeneration and carrying out a screening for substances that are active on this degeneration. A subject of the invention is thus a method in which the cellular element is subjected to a stress prior to being brought into contact with said substance.

The stress can be generated by an axotomy, the application of a toxic compound, for example in a somatodendritic or median axonal compartment of a neuron cultured in the first chamber, a somatodendritic compartment of a cultured neuron contained in the second chamber, for example a neurotoxic, synaptotoxic or axonotoxic compound, a normal, mutated or chimeric protein added to the cell medium, or transferred genetically, or a modification of the physicochemical or physical conditions, for example temperature, pressure or electromagnetic radiation.

In one exemplary embodiment of the method, the first chamber of a device of at least three chambers is seeded with a first neuronal culture enabling axons to extend through the microchannels of the interconnection system toward the second chamber, and then a substance is introduced into the third chamber so as to cause lysis of the axons.

A subject of the invention is also a method for screening a substance presumed to be active, comprising at least the steps of:
  a/ providing a device as defined above, comprising cells cultured according to a method as defined above,
  b/ bringing at least one cell of said cultured cells into contact with at least one substance presumed to be active,
  c/ determining, for said cell, a presence or an absence, or a degree of expression or of activity, of a biomarker of said cell, and
  d/ comparing the determined presence or absence, or degree of expression or of activity of said biomarker with a control value, a range of control values or a control determination.

In such a screening method, the cultured cells can comprise at least two distinct types of cells, in particular neurons, and one cell type can be assigned to each of the first and second chambers of the device.

Said substance to be screened can be introduced into the first and/or the second chamber and/or into the fluidic interconnection system.

Said cells can be neurons.

The method can comprise an additional step a'/, prior to step b/, or an additional step b'/, subsequent to step b, in which the at least one cell of step b/ is subjected to at least one stimulus inducing a cell degeneration process.

Since said at least one cultured cell is a neuron, said stimulus inducing a cell degeneration process can be chosen from a neurotoxic stress, a gene mutation, a viral infection, an axotomy, a toxic molecule chosen from neurotoxic, synaptotoxic or axonotoxic molecules, a normal, mutated or chimeric protein introduced into the cell culture medium or genetically transferred into the cultured cells, an infectious, in particular neurotropic, agent or a modification of a physicochemical condition, in particular chosen from pressure, temperature, pH, osmolarity or an electromagnetic wave, in particular of microwave type or of radiowave type.

The cell degeneration process can be specific for a cell compartment, in particular chosen from the soma, the axon, the dendrites or the synapse.

The substance to be screened can be presumed to prevent, reduce, slow down or treat said cell degeneration.

The biomarker can be a marker for said cell degeneration.

A subject of the invention is also a screening method comprising the following steps:
  a) seeding a device as defined above, with one or more cell types so as to create a cell network,
  b) generating a stress, which can be carried out optionally before step a),
  c) applying a test compound,
  d) determining the effect of the test compound.

A subject of the invention, according to another of its aspects, is also a method for fabricating a microfluidic device in which said microfluidic system is prepared by means of a photogravure technique using a first mask comprising a plurality of micrometric patterns, and superimposing during the photogravure, on said mask, a second overmask which has an optical transparency, corresponding to a subset of said plurality of patterns, in order to transfer only said subset onto the substrate during the photogravure.

The invention enables, according to embodiments, an effective neuronal compartmentalization, the imposition of directionality on the axonal growth, selection between various types of axons, and/or the creation of networks of cells involving various types of cells contained in different chambers, and having directed connections by means of the cell extensions.

The invention can enable the dynamic imposition of certain physical or chemical stimuli on one or more selected cell subcompartments, the specific biolabeling of some of these subcompartments and the analysis of the biological content of some of these subcompartments.

According to one aspect, the microfluidic device of the invention comprises at least two microfluidic chambers for cell culture, the size of which is compatible with the development of cell somas, separated by a microfabricated interconnection zone, the geometry of which can affect the direction, the kinetics, the number, the type and the interconnections of axonal fibers or more generally of cell extensions. Various types of microstructures can be used to this effect, and various examples are proposed below.

Various types of microstructures of the fluidic interconnection system can have various types of effects or exert various types of selection on the growth of the cell extensions, and can be selected and, optionally, combined according to the desired effects.

Structures comprising channels having an asymmetrical narrowing will promote the growth of cell extensions in one direction, generally that which goes from wider to narrower.

Structures comprising microchannels having a twisted course will make it possible to delay, accelerate or select certain particular types of axons belonging to neural subtypes. A subject of the invention is the use of a device comprising such a structure for this purpose.

Structures containing obstacles, for example micropillars, can enable axonal or dendritic compartmentalization, while at the same time making it possible to regulate the formation of inter-axonal connections. A subject of the invention is thus the use of a device comprising such a structure for this purpose.

Another object of the invention is to propose microfluidic devices for culture, comprising, in addition to the above interconnection systems, individual subchambers for cell culture which make it possible to precisely control the positioning of the cell somas. Optionally, these subchambers have a surface treated so as to promote the adhesion of at least one certain type of cell soma.

The invention relates to cells of any type which can, during their multiplication and/or their differentiation, give rise to cell extensions. It relates in particular to stem cells, neuronal cells, neuronal stem cells, and also any cells that can give rise, during their differentiation, to neuronal cells and to specialized neuronal subtypes.

The invention can enable the oriented reconstruction of the simplest to the most complex neuronal networks, optionally involving various neuronal subtypes, and/or a combination of neurons and of non-neuronal cells, and/or various types of axonal and/or dendritic interactions between neurons.

The invention can make it possible to reconstruct and to study the interactions between neuronal cells and non-neuronal cells.

The invention can make it possible to target specific neuronal compartments with reagents and/or medicaments, and to collect biomarkers originating from some of these compartments, for analysis.

The transparent nature of the chambers and of the interconnection systems can facilitate the in situ analysis, optionally in real time, of said cell compartments such as axons, dendrites, synapses or somas, with molecular or cell biology tools, such as, by way of nonlimiting examples, immunohistochemistry, nucleic acid hybridization, nucleic acid amplification, electrochemistry or electrophysiology. The implementation of such studies during neuronal development, in neuronal or pathological states, falls within the context of the invention.

The invention is particularly suitable for comparative studies, high content screening, high throughput screening, the search for medicaments or toxicological studies.

It is also particularly suitable for studying the effect of natural or artificial neurotoxic agents, apoptotic signals, or natural or artificial neuroprotective agents.

In general, it is well-suited to the detailed study of the presence, in specific cell compartments, of biomarkers.

The term "biomarker" is intended to mean any type of information relating to the biological state of a cell. Typical examples of biomarkers commonly used in biology, in cell biology and in medicine, are the presence of a protein, its concentration, its level of expression, the presence or the concentration of a metabolite, of a neurotransmitter, of a nucleotide sequence or of an enzyme, or else the localization of a protein, its spatial distribution in the cell compartment, or any combination of these criteria.

For the purpose of the invention, the term "determining" is intended to refer to a quantitative or qualitative detection.

For the purpose of the invention, the term "control value", "range of control values" or "control determination" is intended to refer to a value, a range of values or a determination of a predetermined parameter under "baseline" or "normal" conditions. Such a condition is usually obtained in the absence of the element of which the effect is to be determined.

For example, with regard to the degree of expression of a biomarker, the control value, the range of control values or the control determination can be a value, a range of values or a determination corresponding to the degree of expression of said biomarker in cells in the absence of stimulus inducing cell degeneration.

According to the invention, these biomarkers can be detected by various optical methods, in particular fluorescence imaging, or electrical methods, in particular electrophysiology.

Many methods are known to those skilled in the art, and in particular to cell biologists and neurologists, for identifying biomarkers in cells. In fact, one of the major advantages of the invention is that of enabling the use, in vivo, of the widest range of methods for detecting and analyzing biomarkers that is known in cell biology and of being able, for the first time, to implement said use on neurons arranged in previously inaccessible architectures.

It will be possible to understand the invention more clearly on reading the detailed description, which follows, of nonlimiting exemplary embodiments thereof, and on examining the appended drawing.

Figure 1:
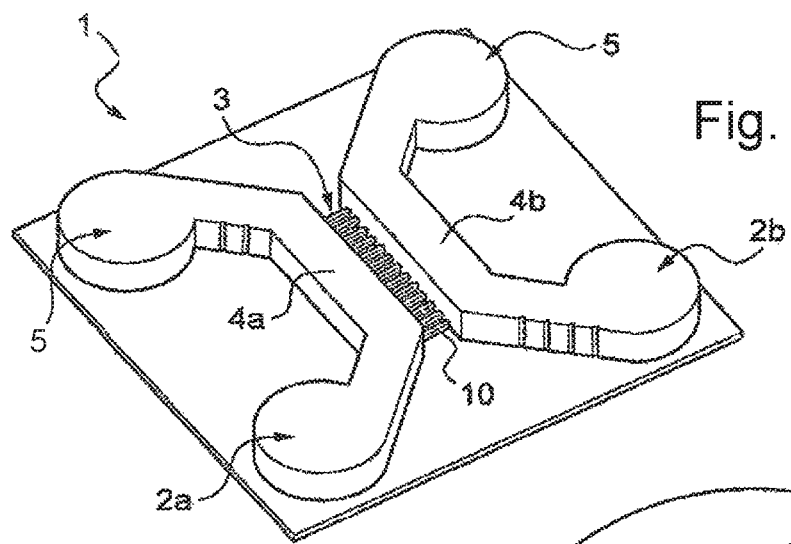
FIG. 1 is a perspective view of an embodiment of a microfluidic device according to the disclosure.

FIG. 1 represents, diagrammatically, an example of a microfluidic device 1 prepared in accordance with the invention, also called "chip".

This microfluidic system 1 comprises, in the example considered, microfluidic chambers 2, of which, in this case, there are two and which are referenced 2a and 2b, intended to be seeded with first and second cell cultures, respectively.

The microfluidic system 1 also comprises a fluidic interconnection system 3 connecting the first and second chambers 2a and 2b and enabling cell extensions to extend from one chamber to the other chamber.

The microfluidic chambers 2 are, for example, produced with two respective parallel portions 4a and 4b between which the fluidic interconnection system 3 extends.

The portions 4a and 4b, also called macrochannels, are, for example, as illustrated, connected at their ends to wider portions 5 (also called reservoirs), for example cylindrical in shape.

The device 1 can be produced on any suitable single-material or multimaterial support. This support can comprise, as illustrated in FIG. 1A, several devices 1 for cell culture according to the invention.

Figure 1A:
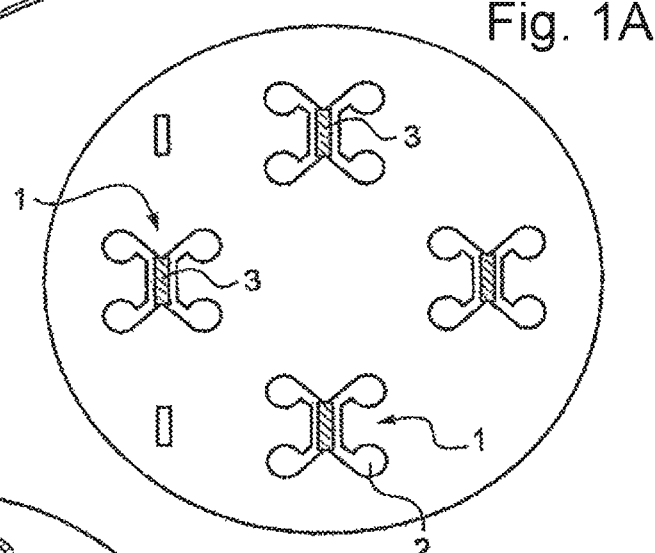
FIGS. 1a and 1b are schematic top views showing substrates having formed on them a plurality of microfluidic devices.

In the example of FIG. 1A, the devices 1 are produced on a basal substrate which is, for example, transparent, being, for example, a circular microscope coverslip, for example 42 mm in diameter. The invention is not limited to one material or to one particular shape.

The material of which the chambers are made is, for example, PDMS, bonded to the glass plate made up of the microscope coverslip for example, or another material which defines the bottom of the chambers.

In order to fill the chambers, the material of which the chambers are made can, for example, be pierced, at the level of the wider portions 5. Holes of 4 mm are, for example, made therein.

A liquid can be introduced into the chambers by means of a pipette or of a perfuser. Between 10 and 100 µl of liquid can, for example, be introduced into each chamber 2a and 2b.

During the use of the device, it is possible for no permanent flow of liquid to exist between the chambers 2a and 2b.

In FIG. 1, the portions 5 are cylindrical, but other shapes are possible.

The devices 1 can be autonomous from the fluidic point of view (fluidically autonomous), i.e., once the various media have been introduced into the chambers, there is no fluidic communication by the device with the exterior.

Figure 1B:
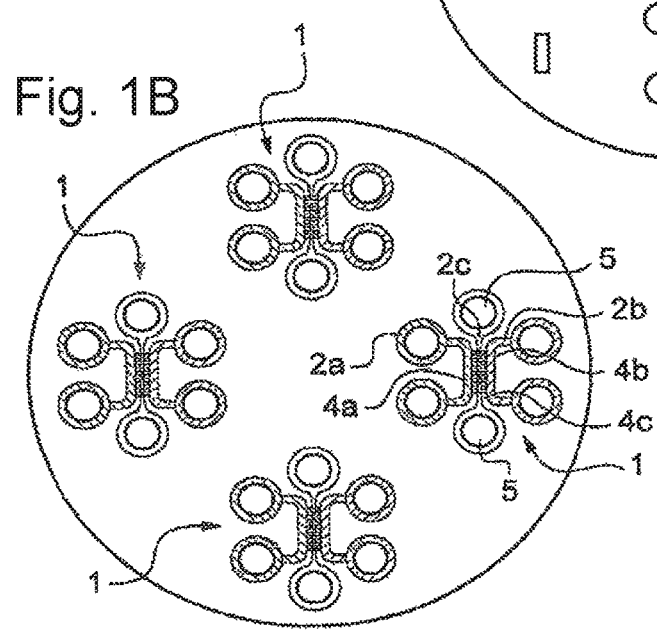

In FIG. 1B, the devices 1 comprise three chambers 2a, 2b and 2c per microfluidic device 1.

The third chamber 2c (also called central chamber, in which case the chambers 2a and 2b can be called distal chambers) comprises a rectilinear portion 4c, also called channel, which extends between the portions 4a and 4b of the chambers 2a and 2b. This portion 4c links two wider portions 5 of the chamber 2c.

The portions 4a, 4b, 4c are, for example, at least 55 µm wide.

In FIGS. 1A and 1B, in the interests of clarity of the drawing, the fluidic interconnection system 3 has not been represented.

The portion 4c can be filled with a liquid which does not hinder the progression of the cell extensions but can limit the diffusion of a compound introduced into one of the chambers to the other chamber.

The portion 4c can also be used to perform an axotomy, by filling it with a detergent for example.

The portion 4c can extend along a longitudinal axis contained in a plane of symmetry for the first and second chambers, but other configurations are possible.

The fluidic interconnection system 3 can be produced in various ways, for the purpose of promoting the progression of at least a first type of cell extension compared with at least a second type of cell extension, the first and second types of cell extension differing, for example, by virtue of the microfluidic chamber from which they originate or by virtue of the cell type of which they are the extension. The progressions can take place, for example, without a stream of fluid in the interconnection system.

In general, the fluidic interconnection system can comprise a plurality of juxtaposed microchannels, which are connected at their ends to the cell chambers, either directly, or by means of single-cell chambers as will be specified below.

The fluidic interconnection system can comprise, for example, between 1 and 1000 microchannels, which may be of various shapes.

All the microchannels of the same fluidic interconnection system can have the same shape, each being, for example, the replica of another, for example by translation or rotation or a more complex geometric transformation.

In one exemplary embodiment of the invention, the fluidic interconnection system comprises a plurality of microchannels of which the longitudinal axes are parallel and, for example, perpendicular to the macrochannels 4a and 4b, or even 4c, of the cell chambers 2 which they connect.

The fluidic interconnection system can comprise microchannels having an asymmetrical shape, in particular when observed from above.

Represented in FIG. 2A is a first example of a microchannel 10 of the fluidic interconnection system 3, having an asymmetrical shape, with a wider portion 10a of width a and a narrower portion 10b of width b, connected via an intermediate portion 10c, having, for example, a width which decreases linearly.

It has been noted, surprisingly, that, by using devices having asymmetrical channels of different lengths, it is possible to select the axons not only according to the chamber from which they originate, but also according to their cell subtype.

For example, using channels at least 1200 µm in length, the neurons of cerebral granules cannot send axons into the distal chamber, whereas the projection neurons can do so.

In addition, it has been observed that axons do no penetrate or penetrate with difficulty into a channel of which the width is less than or equal to 2 µm, which makes it possible to produce fluidic interconnections impermeable to axons.

FIGS. 2B to 2D also represent other possible shapes for the microchannels 10, for example a trapezoidal shape viewed from above, as illustrated in FIG. 2B, a nose cone shape, as illustrated in FIG. 2C, or a horn shape as illustrated in FIG. 2D. The width of the microchannel 10 can vary in linear or nonlinear fashion, when moving along the longitudinal axis of said microchannel.

The microchannels 10 can be formed by grooves in the bottom part of the device, as illustrated in FIG. 2E, or by grooves formed in the top part, as illustrated in FIG. 2F.

The microchannels 10 have, for example, a length of between 10 µm and 10 000 µm, preferably between 50 µm and 2000 µm, for example about 500 µm.

The microchannels 10 have, for example, a thickness of between 1 and 5 µm, for example about 3 µm.

The width of the microchannels 10, in their widest part, is for example between 5 and 100 µm and, in the narrowest part, is between 1 and 10 µm. The width of the microchannels, in the narrowest part, is, for example, at most equal to half their width in the widest part.

In exemplary embodiments, the width in the widest part is 10 µm and that in the narrowest part is 3 µm. With such values, it is possible to observe, surprisingly and spectacularly, a selectivity in the region of 1000, i.e. the cells contained in the cell chamber in contact with the widest part of the microchannel send at least 1000 times more axons than those contained in the cell chamber in contact with the narrow part of the microchannel.

The microchannels of the fluidic interconnection system can each have a rectilinear shape or, as a variant, a nonrectilinear shape.

Represented in FIG. 3A is a microchannel 10 in the shape of a zigzag, with, for example, consecutive portions arranged at right angles to one another. The period L of the zigzag pattern is, for example, between 5 µm and 100 µm, and preferably between 10 and 50 µm.

Represented in FIG. 3B is a microchannel 10 having an undulating shape, composed, for example, of a succession of semicircular portions. According to the neuronal type to be selected, the period L of the undulating pattern is, for example, between 3 and 5 µm, or between 5 and 10 µm, or else between 10 and 30 µm.

Channels of this type can be useful for selecting axon subtypes. For example, using channels with small radii of curvature, it has been observed that cortical axons are stopped, whereas hippocampal axons or striatal axons are capable of passing through these channels.

Represented in FIG. 3C is an example of a microchannel 10 which comprises a succession of widened portions 10a and of narrowed portions 10b. The narrowed portions 10a and 10b are, for example, of constant width, whereas the widened portions have inlets and outlets which are respectively divergent and convergent and a median portion 10c of constant width a, for example between 5 µm and 50 µm. The width b of the narrowed portions 10b is, for example, between 2 µm and 10 µm.

The length d of the narrowed portions 10b is, for example, between 10 and 500 µm. The length c of the inlets and outlets is, for example, between 10 and 500 µm. The length f of the portion 10c is, for example, between 10 and 500 µm.

FIGS. 4A to 4C give examples of an interconnection system 3 of the type consisting of networks of obstacles.

In these figures, it is seen that it is possible to produce obstacles 70, for example in the form of circular islands (also called micropillars), as illustrated in FIG. 4A, or of cobblestones of polygonal shape, for example rectangular shape, as illustrated in FIG. 4B.

The obstacles 70 can have various arrangements, for example be arranged in the form of a network with regular positions in the two dimensions of the plane, as in FIG. 4A or 4B. The obstacles 70 can also be in the form of arrangements where the centers of the islands are arranged like the vertices of polygons, as illustrated in FIG. 4C.

The arrangement of FIG. 4A corresponds to a preferred embodiment, in which it is not possible to circulate between the obstacles 70 a line which does not have a radius of curvature smaller than the radius of the obstacles. Such an arrangement can be used to separate cortical and striatal axons. The values a, b and c are, for example, between 2 and 10 µm, between 2 and 10 µm and between 5 and 100 µm, respectively, and preferably between 2 and 5 µm, between 2 and 5 µm and between 5 and 50 µm.

FIG. 5 gives nonexhaustive examples of arrangements that can be used to form, by means of the invention, complex and oriented neuronal architectures. The small rectangles represent, schematically, chambers 2 for cell culture. The arrows represent, also schematically, the interconnection systems and their directionality. These directed systems can be used, for example, to study axonal growth, synaptogenesis, retrograde and anterograde transport, or cell signaling, or for studying neurodegenerative processes, such as Alzheimer's disease, Huntington's disease and Parkinson's disease, in particular diseases in which specific subtypes of neurons show signs of early synaptic dysfunction.

The fluidic interconnection systems can be arranged in alignment with one another or, as a variant, can be oriented in different directions.

FIG. 22 represents, in b, an example with three chambers 2a, 2b and 2d, the chambers 2a and 2b being connected via a first fluidic interconnection system 3 and the chambers 2b and 2d via a second fluidic interconnection system 3', which is also seen on the image c. The microchannels of the various interconnection systems are perpendicular to one another. The distance between the microchannels of the interconnection system 3 can be different than that between the microchannels of the interconnection system 3'.

The microchannels of the fluidic interconnection system join up, for example, at the elbow which connects the macrochannel of the chamber 2b to the adjacent wider portion 5.

If it is desired to be able to infuse reagents from certain neuronal compartments, or to collect products, without disturbing the neuronal organization, according to one of the variants of the invention, the interconnection system is delimited over at least a part of its surface by a porous wall allowing exchange of molecules and ions with a secondary compartment, but not allowing the exchange of cells with said secondary compartment. This wall can be formed, for example, by inserting a membrane between two layers of material constituting, respectively, the bottom part and the top part of the channel, and by reserving, in the top part, a secondary channel, in contact with said membrane, and capable of supplying or collecting products.

According to other embodiments, this membrane can be formed in situ, for example by photopolymerization.

Finally, it can also be made up of a network of very close obstacles, for example having a distance of less than 2 µm, which does not allow axons to pass.

Represented in FIG. 6A is an example of a microchannel 10 with a bifurcation which comprises a first portion 50 which joins up with two branches 51. The portion 50 can have a width a, as can the branches 51. The patterns with bifurcations enable, for example, axonal connection or division. The longitudinal axes of the branches 51 are, for example, separated, at the end opposite the inlet end of the portion 50, by a distance L. The longitudinal axis of the portion 50 is, for example, contained in a median plane with respect to the branches 51. The latter can comprise two portions 52 which diverge, for example over a length of 100 µm.

Represented in FIG. 6B is a table of values for the parameters a and L for various examples of configurations A to E.

In FIG. 6C, the microchannel 10 is produced with a portion 50 of which the width 2a is, for example, double that of the branches 51. The table in FIG. 6D gives some examples of values for the width a, in various configurations A to C.

FIG. 6E represents a microchannel 10 comprising a portion 50 which narrows before splitting into two branches 51. The portion 50 goes, for example, from a width a to a width b and the branches 51 are, for example, the same width as that of the narrow portion 54.

The length of the convergent portion 55, via which the portion 50 joins up with the narrow portion 54, is for example 100 µm.

The table in FIG. 6F gives various examples of the a/b ratio for various configurations A to C. The presence of the narrow portion 54 makes it possible to focus the bundle.

The configuration of FIG. 6C makes it possible to preserve the flow rate. The stress on the filopodium is a priori greater than in the example of FIG. 6A, which makes it possible to hope for splitting thereof.

FIG. 6G presents a configuration having properties similar to those of FIG. 6C with regard to the mechanical stresses on the Y-shaped zone. The configuration of FIG. 6G also makes it possible to test the behavior of axon bundles which cross.

In the configuration of FIG. 6G, the microchannels 10 comprise parallel rectilinear portions 60 which join up with branches 61 which diverge and then converge so as to join up with a new rectilinear portion 60.

Two branches 61 of two adjacent channels join up at 63, the branches bringing about, between them, an island 64. The distance between the longitudinal axes of the rectilinear portions 60 is, for example, 30 μm and the pitch in the longitudinal direction is, for example, 100 μm. The width of a portion 60 is, for example, double, equal to 2 a, that of a branch 61.

The table in FIG. 6H gives various examples of values of the width a in configurations A to C.

Illustrated in FIG. 7 is the possibility of producing single-cell chambers 80 between the chambers 2. The single-cell chambers 80 communicate, for example, with an end 90 of an associated microchannel 10 and, on the opposite side, with a linking channel 92 of which the cross section is greater than that of the microchannel which joins up directly with the chamber 2. The chamber 2 has a height of, for example, 55 μm, the single-cell chambers 12 μm and the microchannels 10, 30 μm.

The single-cell chambers 80 can trap the somas of the neurons in front of the entry of the microchannels. In order to produce these structures, a third layer of resin can prove to be necessary. Their characteristic size could range from 10 to 100 μm so as to receive one or more somas.

With regard to the fabrication of the devices according to the invention, many microlithography methods can be used, for example those described by Patrick Tabeling. Introduction to microfluidics. Belin.

According to one preferred embodiment, the device is fabricated by means of methods of soft lithography, as described in Whitesides, G. M.; Ostuni, E.; Takayama, S.; Jiang, X.; Ingber, D. Soft lithography in biology and biochemistry., Annu. Rev. Biomed. Eng. 2001, 3, 335-373. It is possible to use an elastomer, PDMS (polydimethylsiloxane), which, once crosslinked, has properties that are very suitable for cellular and molecular biology: transparent, not very reactive, biocompatible.

PDMS is not a surface to which neurons naturally adhere. Regardless of the culture environment (Petri dish or microfluidic chip), it may prove to be useful to chemically treat the surface. The means most commonly used consists in using polylysine, which adsorbs to the walls and enables cell adhesion. It is also possible to use other adhesion proteins, such as fibronectin or collagen, but these substances do not naturally adsorb sufficiently to PDMS to enable cell adhesion, unlike polylysine. It may be necessary to chemically bond them to the PDMS. It is therefore possible to use a photoactivable crosslinker 2: when said crosslinker receives UV radiation, the energy received allows it to create a bond with the PDMS. Many crosslinkers can be used in the invention, such as, by way of nonlimiting examples:

Sulfo-sanpah: sulfo-sanpah (N-sulfosuccinimidyl 6-[4'-azido-2'-nitrophenylamino]hexanoate) is a molecule which has, at one of its ends, a photoactivatable nitrophenyl azide group, and at the other end, an N-sulfosuccinimidyl ester group which has the particularity of being very reactive with amine functions (amidation), which are very common in proteins.

Benzophenone and BBTA: benzophenone is a radical initiator which strongly adsorbs to PDMS. When it is photoactivated, it can create a bond with a molecule containing hydrogens and thus graft it onto the surface. BETA ((4-benzoylbenzyl)trimethylammonium) is a hydrophilic version of benzophenone, but its function is a priori the same, except that it can be dissolved in the same solution as proteins since it is hydrophilic.

The reaction takes place while the two molecules are in water, unlike benzophenone, which must first be adsorbed onto the PDMS.

According to one preferred embodiment, which is useful in particular in conjunction with the applications in which it is desired to promote the adhesion of specific cells or cell compartments to specific sites, localized photoactivation can be used.

It is, for example, possible to use a mask so as to UV-illuminate only at desired sites, in order to create adhesion protein patterns as described in Jenny Fink, Manuel Théry, Ammar Azioune, Raphael Dupont, Francois Chatelain, Michel Bornensa and Matthieu Piel. Comparative study and improvement of current cell micro-patterning techniques. Lab on a Chip, 2007, 7, 672-680.

According to another preferred embodiment, photoactivation by microscope can also be used: by sending UV rays through a microscope, it is possible to project them onto the PDMS surface of the microfluidic chip, as described, for example, in Jun Nakanishi, Yukiko Kikuchi, Tohru Takarada, Hidekazu Nakayama, Kazuo Yamaguchi, and Mizuo Maeda. Photoactivation of a Substrate for Cell Adhesion under Standard Fluorescence Microscopes. J. AM. CHEM. SOC. 2004, 126, 16314-16315. By placing a photomask with the desired patterns in the object focal plane of the microscope, the desired patterns are obtained on the surface of the microfluidic channels. Furthermore, the objective makes it possible to considerably narrow the size of the patterns of the photomask, thereby making it possible to gain in terms of precision.

Some interconnection structures require a resolution of about 1 μm. Consequently, it is desirable to use a mask made of high-resolution quartz. In order to make this support as profitable as possible, it is also part of the objectives of the invention to propose a novel lithography method facilitating its use. According to this method, the entire surface of a quartz mask 120, for example as represented in FIG. 8, is etched with a multiplicity of patterns of microchannels and of cell chambers. This tool makes it possible, in a single mask, to explore patterns which could be advantageous in the development of a controlled network of neurons, or make it possible to test certain properties of axonal projections, such as their bundling/unbundling property or their behavior in rounded channels.

This mask 120 has two purposes:
To make it possible to lithograph at the same time four different microstructures in a standardized manner. It has been designed so as to have maximum compatibility with the various macrochannel geometries, and can therefore be used for all the geometries, which offers great flexibility of use.
To place the most number of different patterns on the same quartz mask (which is quite expensive).

A multiplicity of patterns (96 in the example given in FIG. 8) can be juxtaposed next to one another (the distances have been standardized). Alignment patterns have been arranged at its center. It can therefore be used to make chip patterns having many compartments, as long as the resin used for the microstructures is a negative resin. 13 microchannel shapes and six cell compartment shapes have been etched on the mask 120. Each shape has been reproduced with various sizes, bringing the number of patterns to 96.

Multi-scale patterns have, moreover, been etched. These patterns group together, in one go, various sizes and shapes, the aim being to explore a maximum number of shapes in a minimum number of experiments. For example, for the narrowing channels, a multi-scale pattern has been designed which makes it possible to determine, in a single experiment, which size is favorable for a given type of neuron.

By way of example, a total of 96 different patterns represented in FIG. 8 can be produced using a single high-resolution mask. The selection between the various patterns can be carried out by means of an overmask 130 which has a lower resolution and which has windows 110, as represented in FIG. 10.

FIG. 9 represents two examples of patterns that can appear through a window 110.

The overmask 130 can also comprise alignment patterns 135.

The invention can be used advantageously for culturing and studying various types of cells, being particularly advantageous for working on neurons.

Neurons are cells which, once differentiated, no longer multiply. It is therefore impossible to propagate neuron cell cultures. It is, moreover, important to obtain these neurons during their neurogenesis peak: this is the moment where neuron proliferation ends and where differentiation is carried out. Moreover, they are not yet mature, i.e. their axons and their dendrites have not yet grown, and it is therefore possible to seed them into culture dishes or chips.

Advantageously, neuronal material taken from animals, and in particular from mice, according to dissection protocols well known to those skilled in the art, will be used in the devices according to the invention.

The invention also makes it possible to visualize cells and to localize substances within specific cell compartments. The invention lends itself particularly well to all the immunolabeling, immunohistochemistry, DNA labeling, fluorescent labeling, luminescent or chemiluminescent techniques.

Given below, by way of example, is a list of advantageous molecules for cell biology, which can be detected by fluorescent immunolabeling in devices according to the invention:

α-tubulin: this tubulin subunit is present in all cell microtubules.
This labeling therefore makes it possible to see all of the cytoskeletons of the cells present in the compartment.
β3-tubulin: subunit specific for the microtubules of axons, without exception.
Map2: Map2 is associated with microtubules. It is especially present in dendrites.
Synaptophysin: when an axon has no synapse, synaptophysin is present homogeneously in the axon. It accumulates in the synapses when the latter mature and connect to a neuron.
p-erk: erk (extracellular regulated kinase) is a protein kinase which, when it is activated, is phosphorylated and then translocated into the nucleus. Its activation occurs in the glutamatergic signal transduction cascade of striatal neurons. It is possible to verify, by means of this labeling, that the striatal neurons have indeed been activated by glutamate.

Nonimmunological labeling can also be used. For example, DAPI or any other DNA-intercalating agent, which makes it possible to visualize the cell nuclei, can be used in the devices according to the invention.

FIG. 11 is a photograph of an exemplary embodiment of an interconnection system comprising microchannels of which the width decreases from one microfluidic chamber to the other. In FIG. 11, the somatic compartment where the cortical neurons were seeded is seen on the left. The axons pass through the microchannels 10, the width of which goes, for example, from 15 µm at the inlet to 3 µm at the outlet.

It is seen on the photograph that, on the left, the cortical neurons project axon bundles in the wide part of the microchannels, whereas, on the right, the cortical axon bundles, indicated by dashed arrows, emerge from the narrowed side and connect to the somas and to the striatal axons indicated by continuous-line arrows.

FIG. 12 shows, on the left-hand photograph, the outlet of the narrowest microchannels, in 40× phase contrast, with a cortical culture alone, and, on the left-hand photograph, in the case of a coculture. In the latter case, the network of cortical axons is much more diffuse and entangled.

Figure 1C:
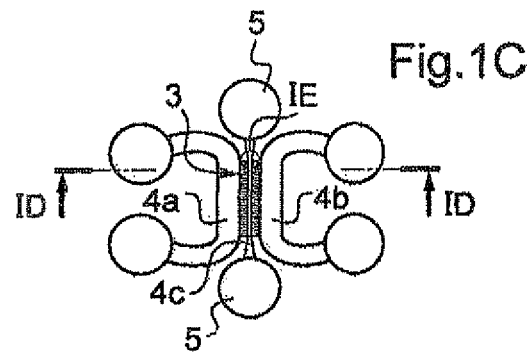
FIG. 1C is an example of a device similar to those represented in FIG. 1B.
Figure 1E:
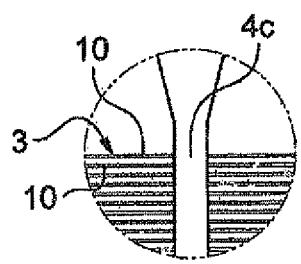
FIGS. 1E and 1F represent the details IE and IF of FIGS. 1C and 1D.
Figure 1D:
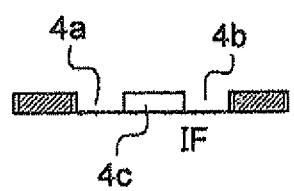
FIG. 1D is a section along ID-ID of FIG. 1C.
Figure 1F:
Figure 1G:
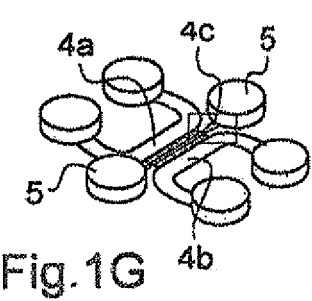
FIG. 1H represents a detail of FIG. 1G, which is a perspective view of the device of FIG. 1C.
Figure 1H:
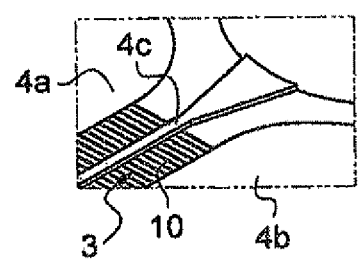

Represented in FIG. 1C is an example of a device similar to those represented in FIG. 1B. FIG. 1D is a section along ID-ID of FIG. 1C. FIGS. 1E and 1F represent the details IE and IF of FIGS. 1C and 1D. FIG. 1H represents a detail of FIG. 1G, which is a perspective view of the device of FIG. 1C.

The portion 4c may be of use for reducing the risk of a chemical substrate migrating from one macrochannel 4a or 4b to the other.

In one example, the length of the interconnection system 3, measured perpendicularly to the microchannels, is for example between 3 mm and 5 mm, and is, for example, 4 mm.

The width of a macrochannel 4a or 4b is, for example, between 500 and 1500 µm and is, for example, 1000 µm. The width of the portion 4c is, for example, in its region intersecting the microchannels, between 50 and 150 µm, being for example 100 µm. The width of a macrochannel 10 is for example 10 µm at its arrival at the start of the portion 4c.

The height of the microchannels 10 is for example less than or equal to 5 µm, being for example 3 µm. The height of the portion 4c is for example less than 100 µm, being for example 55 µm.

EXAMPLES

The microfluidic devices used in the examples hereinafter may be as described with reference to FIG. 1A or 1B.

The devices used can be composed of at least two culture chambers (4a and 4b) separated by microchannels (3) for example. Each macrochannel of a chamber is connected to the widened portions forming a reservoir (5), which are for example perforated through the elastomer in the case where they are made of PDMS.

Each device is for example replicated four times on the same substrate, as illustrated in FIG. 1A, which represents four independent devices each with two chambers.

FIG. 1B represents four independent devices each with three chambers (these chambers still being sometimes called compartments).

The two (or three or more) culture chambers are separated by interconnection systems with microchannels or other microstructures.

More specifically, the following devices were used:
Device D1 (FIG. 19):
The device comprises two culture chambers of dimensions (L×l×h in µm) 4500, 1000, 55, interconnected via 167 narrowing microchannels (also called diodes) which have a length of 500 µm, and a width of 15 µm on the wide side and 5 µm on the narrow side, and a height of 3 µm. Each macrochannel is connected to two reservoirs (widened portions) which have a diameter of 4 mm and a height between 5 and 10 mm. The chambers are attached to glass coverslips 170 µm thick.

Device D2 (FIGS. 13, 14, 15, 16, 17):

Two culture chambers of dimensions (L×l×h in μm) 4500, 1000, 55 are interconnected via 167 narrowing microchannels (also called diodes) which have a length of 500 μm, and a width of 15 μm on the wide side and 3 μm on the narrow side, and a height of 3 μm. Each chamber (macrochannel) is connected to two reservoirs (widened portions) which have a diameter of 4 mm and a height of between 5 and 10 mm. The chambers are attached to glass coverslips 170 μm thick.

Device D3 (FIGS. 11, 12, 18):

Two culture chambers of dimensions (L×l×h in μm) 4500, 1000, 55 are interconnected via 167 narrowing microchannels (also called diodes) which have a length of 500 μm, and a width of 15 μm on the wide side and 2 μm on the narrow side, and a height of 3 μm. Each chamber (macrochannel) is connected to two reservoirs which have a diameter of 4 mm and a height of between 5 and 10 mm. The chambers are attached to glass coverslips 170 μm thick.

Device D4 (FIGS. 20, 21):

Three parallel culture chambers, namely two distal chambers of dimensions (L×l×h in μm) 4500, 1000, 55 and one central chamber (4500, 100, 55), are interconnected via 167 microchannels which have a length of 500 μm, and a width of 15 μm on the wide side and 3 μm on the narrow side, and a height of 3 μm. Each chamber is connected to two reservoirs (widened portions) which have a diameter of 4 mm and a height of between 5 and 10 mm. The chambers are attached to glass coverslips 170 μm thick. Some devices were prepared using narrowing microchannels allowing passage "in series" and which have a length of 500 μm, a width of 15 μm on the wide side and 3 μm on the narrow side, and a height of 3 μm. Some devices are produced with a central chamber (L×l×h in μm) 4500, 50, 3, separated from the other two chambers by microchannels 250 μm long, which are straight or narrowing (15 μm×3 μm×3 μm).

Device D5 (FIGS. 22, 23):

These are devices with three or four chambers, the first of which is oriented perpendicularly to the other two. The chambers all have the dimensions (L×l×h in μm) 4500, 1000, 55. The first chamber (A) is connected to the second (B) via a series of 100 microchannels which have a length of between 500 and 1000 μm and a cross section of 10 μm×10 μm×3 μm. These microchannels join up with the second chamber via its perpendicular side. The second (B) and third (C) chambers are connected to one another via 167 microchannels which have a length of 500 μm and a cross section of 10 μm×10 μm×3 μm. Some devices were produced with narrowing microchannels of 15 μm×3 μm×3 μm. Some devices had four chambers, the chamber (B) being connected, according to the same principle, to two perpendicular chambers (A) and (A') located on either side of the chamber (B).

Device D6 (FIG. 24):

The device comprises three parallel culture chambers, namely two distal chambers of dimensions (L×l×h in μm) 25000, 1000, 55 and one central chamber (25000, 3000, 55), interconnected with each of the distal chambers via 930 microchannels which have a length of 250 μm and a cross section of 15 μm on the wide side and 5 μm on the narrow side, and a height of 3 μm.

The two series of microchannels converge toward the central chamber. Each chamber (macrochannel) is connected to two reservoirs (widened portions) which have a diameter of 4 mm and a height of between 5 and 10 mm. The chambers are attached to glass coverslips 170 μm thick.

Example 1: Resin Masters for the Fabrication of Devices According to the Invention Two layers of resins are used in order for the master to have structures of two different thicknesses, namely 3 μm and 55 μm. The microchannels are produced with SU8 2002 resin (Microchemicals) and the macrochannels (thickness 55 μm) with a laminating negative resin SY355 (Microchem).

The two photolithography masks for producing the resin master of the microfluidic channel are designed using the QCad software. Glass slides (1 mm thick, 52 mm in diameter, Ediver, France) are washed with isopropanol, soaked in a piranha mixture (50% $H_2O_2$, VWR International, 50% $H_2SO_4$, VWR International) for 30 minutes and then dried at 150° C. for 2 hours. The slides are plasma-treated for 30 s. The SU8 resin is spread on the slide at a speed which determines its thickness (http://www.microchem.com/products/pdf/SU8_2-25.pdf). Pre-curing on a hotplate follows the spreading in order to eliminate the solvent remaining in the resin. The resin is then insolated for 8 seconds with UV radiation (Karl Suss MJB3 aligner) through a 3 mm quartz support. Post-curing enables crosslinking of the resin. The development is carried out in the developer suitable for the resin, until the appearance of the patterns. The substrate is rinsed at the end of the protocol. A final re-curing makes it possible to reinforce the adhesion of the resin to the substrate and to harden the structures, while finishing off the crosslinking. It is then necessary to deposit the second resin. The slides are preheated at 80° C. The resin film is laminated onto the slides, at 65° C., insolated with UV radiation for 10 sec with the mask for the macrochannels, and then developed. The process is finished by rinsing with isopropanol.

Example 2: Method for the Fabrication of the Devices

The devices are fabricated in two steps.
1) Molding of PDMS: the molding of the device is carried out by pouring PDMS, with 1:10 w/w of crosslinking agent (Sylgard 184, Dow Corning), into a PTFE mold containing the master. The whole is then left to crosslink for 4 hours in an oven at 65° C. The holes in the reservoirs are then made using a punch 4-5 mm in diameter.
2) Adhesive-bonding of the chip: in order to seal the device, a glass slide is adhesive-bonded to the PDMS chip. For this, the two surfaces are carefully cleaned with isopropanol, and then air-plasma treated (PDC-32G, Harrick) for 45 seconds, and then the chip and the glass slide are brought into contact.

Example 3: Surface Treatment

Various examples of surface-treatment of the substrate of devices according to the invention (for example glass slides), in order to facilitate the adhesion of neurons or the progression of axons, are described here.

In the protocol described below, the protein used is fibronectin made fluorescent by grafting of FITC. However, these protocols can be used as they are for functionalizing the slides with other advantageous molecules for one particular application or another.

Preparation of the PDMS Slides:

Firstly, glass slides 4 cm in diameter (Edriver) are cleaned with isopropanol. Then, PDMS comprising 10% of crosslinking agent is deposited on the slide and spread by rotation at 1000 rpm. The slides are then placed in an oven at 65° C.

for at least 2 hours. The slides are then treated with one of the following three protocols:

The slides are plasma-treated for 45 seconds and are used immediately. They then retain both a radical and hydrophilic nature.

The slides are plasma-treated and are stored for a minimum of 4 h in contact with water. They thus lose their radical nature but retain their hydrophilic nature.

The slides are not plasma-treated and therefore have a hydrophobic surface.

Sulfo-sanpah treatment: Solid sulfo-sanpah (Pierce) is diluted to 250 μg/ml in a solution of HEPES (50 mM at pH 8.5). It has a vivid red color. 200 μl of sulfo-sanpah is deposited on the slide and insolated under a UV lamp until the solution turns black (5 min). The slide is washed twice with HEPES with agitation on a shaker for 15 min. A drop of the fibronectin-FITC solution diluted to 0.2 mg/ml in PBS is deposited on the slide, which is placed in a Petri dish kept moist using a wipe soaked in water. The slide is left at 4° C. overnight, before being rinsed with 1×PBS so as to be used.

Benzophenone treatment: a slide is placed in a solution of benzophenone comprising 10% of water/acetone for 1 min and then rinsed with acetone. A drop of fibronectin-FITC solution diluted to 0.2 mg/ml is deposited onto the slide, which is UV-illuminated in the same way as for the sulfo-sanpah, for 20 min. The slide is then rinsed with PBS.

BBTA treatment: the solution of BBTA at 62 mM is supplemented with 0.25 mg/ml of fibronectin-FITC solution and 0.25 mg/ml of natural fibronectin. The slide is exposed to UV radiation, then rinsed with PBS buffer.

Example 4: Primary Culture and Seeding of Neurons

Cerebellar Granule Neurons (CGNs)

The cerebella are removed from young mice of the Swiss line, aged 5 to 7 days. After having decapitated the entire litter, three incisions are made on the back of the head in order to free the cerebellar hemispheres. They are then surgically removed, and placed in a Petri dish containing PBS (Gibco). Once the meninges have been removed, the cerebella are finely cut up, rinsed three times with PBS and dissociated with trypsin-EDTA (Gibco) for 10 minutes at 37° C. The trypsin is then inhibited by adding 10% FCS. The cells are resuspended in a solution of DMEM Glutamax I in the presence of 5 U/ml of DNAse 1 (sigma), and then mechanically dissociated using a 10 ml pipette. After three centrifugations of 6 minutes at 80 g, the pellet is resuspended at a density of 50 million cells per ml, in DMEM Glutamax (Invitrogen), containing 10% fetal calf serum (Biochrom), streptomycin/penicillin (Gibco), and 25 mM of KCl, and supplemented with the neuronal supplements N2 and B27 (Gibco). The cells are then seeded into the somatic compartment of the device. 10 μl of the cell suspension are introduced into the top reservoir of the somatic compartment. The cells then rapidly flow into the compartment and after about 10 seconds, cell-free complete medium is added to the other reservoir so as to stabilize the stream created by the difference in hydrostatic pressure, and thus to allow the cells to adhere to the support. The speed of the stream and the quality of the seeding are controlled using a microscope. About ten minutes after seeding, the four reservoirs (somatic and distal) are filled with complete media (approximately 50 μl/reservoir). Between 20 and 30 000 cells are thus seeded into the distal compartment. The chips are placed in a Petri dish containing 2 to 3 ml of water so as to avoid evaporation of the medium. The culture medium is completely renewed every 2-3 days, over a period which extends over 12 days in vitro (DIV). After two days of culture, the neurons begin to differentiate, emitting neurites in the distal compartment. Approximately 2% of the neurons seeded project their axons into the microchannels. After 4 to 6 days of culture, the axons inserted into the microchannels join up with the distal compartment, so as to reach a total length of 750 to 1200 μm after 10 days and no longer vary with time.

This experiment was carried out with the device D1.

Primary Culture of Cortical and Striatal Neurons.

The cortices and the striata of 14-day-old mouse embryos are removed from the Swiss line.

The tools are the same as for the CGNs. Both hemispheres are removed after having cut the circumference of the cranium. The cortex and the striatum can be removed simultaneously. The cells are subsequently dissociated enzymatically and then mechanically in L15 medium, before being seeded into the culture devices according to the same protocol as that used for the CGNs. The culture medium is composed of Neurobasal containing 2 mM of Glutamax-I, streptomycin and penicillin and, finally, of the culture supplements N2 and B27. After 2 days of culture, the cortical neurons begin to differentiate, projecting neurites, some of which begin to enter the microchannels. Approximately 2% of the cortical neurons seeded project into the microchannels.

Example 5: Protocols for Immunofluorescence Study of the Cultures

All the incubations are carried out at ambient temperature and a stream is generated in order to be able to treat the entire circuit (microchannels). At the desired analysis time, the cells are fixed with 4% paraformaldehyde in PBS for 20 min. After rinsing with PBS, they are permeabilized with 0.1% triton X-100 for 10 min and saturated for 40 min with a solution of PBS containing 1% BSA. After rinsing, the cells are incubated in the dark in the presence of a dilution of primary antibodies of interest for 40 min at ambient temperature. After rinsing with PBS, the secondary antibodies directed against the immunoglobulins (IgGs) of the species that was used to generate the first antibody, diluted in a solution of DAPI, are added for 25 min in the dark. After rinsing with PBS, the chips are subsequently sealed with "fluoromount" mounting medium. The primary antibodies directed against the following proteins of interest were used: β-tubulin (monoclonal ⅓₀₀th, Sigma), α-tubulin (monoclonal ⅓₀₀th, Sigma), Map 2 (rabbit polyclonal, ⅓₀₀th, Chemicon), synaptophysin (monoclonal ¼₀₀th, Sigma).

The anti-species secondary antibodies coupled to Alexa 350, 488 or 555 were diluted to ⅕₀₀th. The following probes were used: phalloidin coupled to cy3 (¹⁄₇₀₀th, Sigma), Mitotracker red (Molecular probes). The image acquisitions are carried out using an Axioberver Z1 microscope (Zeiss) equipped with a 12-bit cooled CCD camera (Coolsnap HQ2, Ropert Scientific), the whole being controlled by the Micro-Manager open source software. The images are processed using the Image J software.

Example 6: Culture of Cerebellar Granule Neurons in a Device According to the Invention The freshly dissociated CGNs are seeded into the somatic compartment. Unlike the conventional cell culture devices where all the cells introduced into a culture well adhere, the number of cells seeded into the microfluidic circuits can be estimated only after counting, under a microscope, the number of cells that have adhered. It thus appears that the cell density in the somatic compartment is approximately 20 000 to 30 000 cells according to the experiments.

After 2 days in vitro (DIV), the neurons begin to establish a complex network of neurites in the somatic compartment, some of which begin to penetrate into the first third of the microchannels. At 4 DIV, the whole of the 150 microchannels is entirely occupied by axons extending into the channels.

The distal compartment is gradually invaded by the neurites. Starting from 7 DIV, neurite growth ends and the axons reach their size, which is from 750 to 1200 µm from the soma, and no longer vary with time.

In the prior art systems, neurite growth takes place equally, whether the right-hand compartment or the left-hand compartment is seeded.

One of the advantages of the invention is to manage to obtain cocultures for which the neuronal projections are controlled (where cortical neurons project onto striatal neurons, for example). One neuronal type is therefore seeded into the left-hand chamber, and another neuronal type into the compartment in the right-hand chamber. In order for the projection to be controlled, it is important for the axons to be able to pass through the microchannels in one direction and not in the other. In this example, microchannels according to the invention of similar shape to that represented in FIG. 2B, with a width of 15 µm on the somatic side and 3 µm on the distal side, for a length of 500 µm, were used. Thus, the axons on the narrowed side do not enter the channels, whereas the axons on the wide side can nevertheless pass through if they are focused. The axons pass through the microchannel only in one direction.

Cortical axons: when cortical neurons are seeded on the wide side (15 µm), 8 to 10 cortical axons cross per microchannel (1000-1500 over the entire system). When they are seeded on the other side, only 5 to 10 axons cross the chip as a whole.

Striatal axons: the cortical axons enter on the large side (15 µm) of the narrowing channels, but they do not manage to cross the part which is 3 µm wide. These microchannel dimensions are therefore particularly suitable for a coculture in which the projection of the cortical axons onto striatal neurons is controlled, and shows that the invention can also be used for selecting axon growth according to cell type.

Example 7

Application to Corticostriatal Coculture and to the Formation of Oriented Neuronal Networks.

Principle: by seeding the left-hand chamber with mouse primary cortical neurons and the right-hand chamber with striatal neurons (3 days later), and using a culture medium suitable for both neuronal types, a one-directional neuronal projection of the cortical neurons onto the striatal neurons could be observed on the 6th day.

This experiment was carried out with the device D2.

Corticostriatal networks: cortical and striatal neurons are taken, by microdissection, from Swiss mouse embryos, the age of which was 14 days of gestation. All the dissection steps are carried out in PBS buffer supplemented with 0.1% glucose. The microdissected structures are digested by incubation in a solution of trypsin-EDTA and dissociated mechanically with a pasteur pipette. After several rinses, the single-cell suspensions are counted. The cortical neurons are resuspended at $40 \times 10^6$ cells/ml in DMEM medium, the striatal neurons being suspended at $15\text{-}20 \times 10^6$ cells/ml. The cortical and striatal neurons are then seeded into their respective culture chamber, the cortical neurons on the wide side of the microchannels of the interconnection system. The culture reservoirs are then filled with culture media composed of DMEM containing glutamax, penicillin and streptomycin and neuronal supplements B27 and N2. The seeded microfluidic devices are then placed in an incubator at 37° C. The culture medium is renewed every 3 days.

It was seen that, with a device according to the invention having an asymmetry in terms of width between the two sides of the interconnection system, cortical-striatal coculture was facilitated. It may be useful, in this coculture experiment, to verify that the projection of the synapses of the cortical neurons onto the striatal neurons is indeed functional.

Orientation of the cortical axon bundle: the growth of the cortical axon bundles is very sensitive to the presence of striatal neurons: they orient themselves very clearly toward them.

Synapse maturation: using synaptophysin labeling, it is verified that the proximity of the striatal neurons indeed brings about sprouting of the synapses of the cortical axons having passed through the microchannel. Maturation of the cortical neuron synapses can be seen in one case but not in the other.

Example 8: Filtration of Hippocampal and Cortical Neurons

Figure 13:
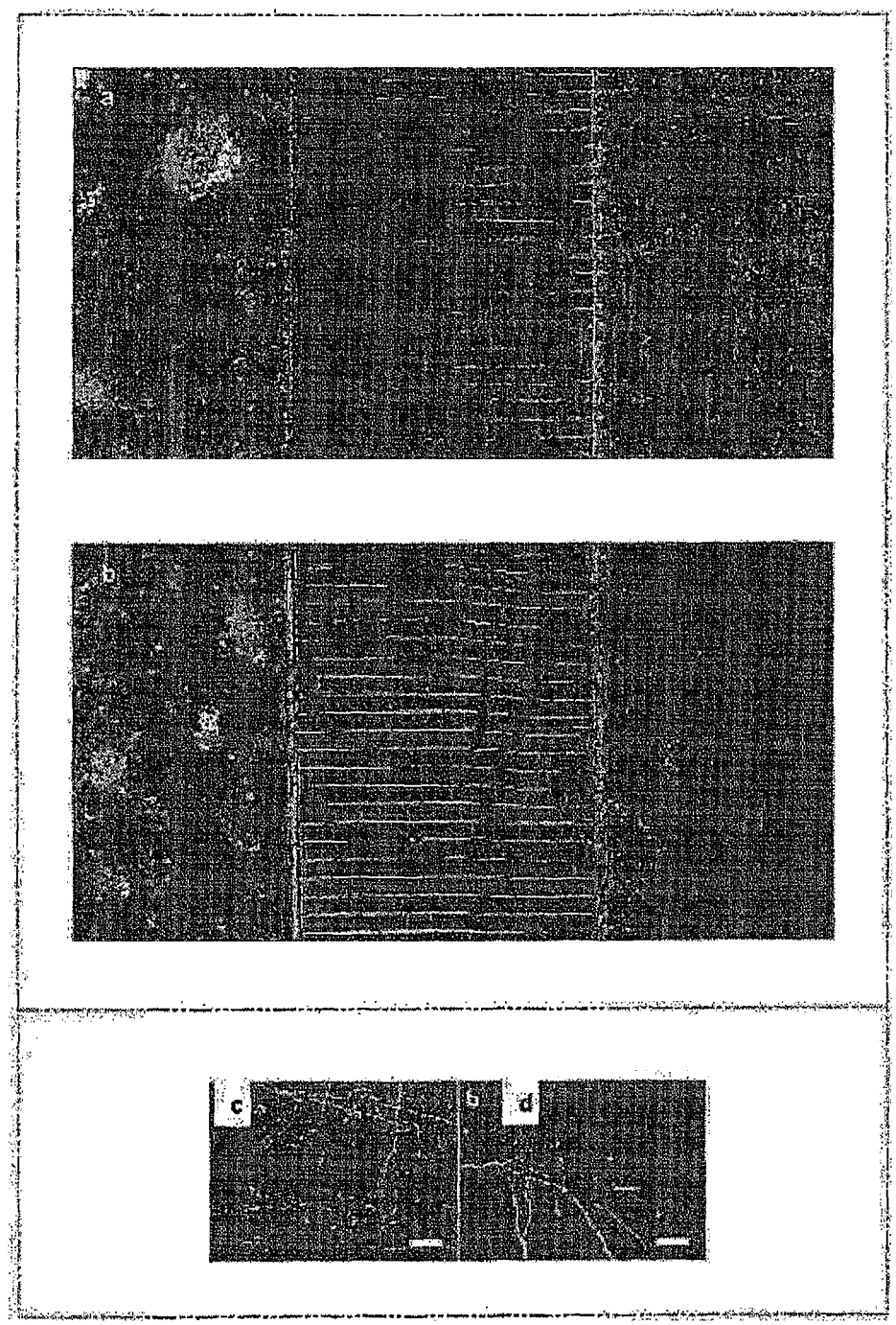
FIG. 13 comprises photographs illustrating the filtration of the axons of hippocampal neurons by a device according to the invention.

FIG. 13 comprises photographs illustrating the filtration of the axons of hippocampal neurons by a device according to the invention.

This experiment was carried out with the device D2.

Figures a and b illustrate the filtration of cortical neurons by asymmetrical microchannels, also called axonal diodes. Top image a: the cortical neurons are seeded on the wide side of the microchannels. The neuronal nuclei are stained blue (nuclear dye, Dapi) and the axonal extensions are in green (beta-tubulin). Invasion, by the axons, of the right-hand chamber can be noted. Bottom image b: the cortical neurons are seeded on the narrow side of the microchannels, only a few axons pass through. The photograph c represents hippocampal axons exiting on the narrow side of the microchannels when the cells are seeded on the wide side. Five microchannel outlets are apparent. The photograph d represents hippocampal axons exiting on the wide side of the microchannels when the neurons are seeded on the narrow side (five microchannel outlets are visible, only one is occupied). (Scale bars 25 µm).

Example 9: Reconstitution of Neuronal Networks in a Device According to the Invention and Visualization of the Synaptic Connections in Corticostriatal Networks and Cortico-Hippocampal Networks. Evaluation of Synaptic Functionality This experiment was carried out with the device D2.

Corticostriatal networks: cortical and striatal neurons are removed, by microdissection, from Swiss mouse embryos, the age of which was 14 days of gestation. All the dissection steps are carried out in PBS buffer supplemented with 0.10 of glucose. The microdissected structures are digested by incubation in a solution of trypsin-EDTA and dissociated mechanically with a pasteur pipette. After several rinses, the single-cell suspensions are counted. The cortical neurons are resuspended at $40 \times 10^6$ cells/ml in DMEM culture medium, the striatal neurons being suspended at $15\text{-}20 \times 10^6$ cells/ml. The cortical and striatal neurons are then seeded into their respective culture chamber, the cortical neurons on the wide side of the microchannels. The culture reservoirs are then filled with culture media composed of DMEM containing glutamax, penicillin and streptomycin and neuronal supplements B27 and N2. The seeded microfluidic devices are then placed in an incubator at 37° C. The culture medium is renewed every 3 days.

Photograph 1a of FIG. 14 represents microfluidic devices for neuron culture according to the invention, comprising two individual culture fields interconnected via a series of asymmetrical microchannels, some of which are visible on photograph 1b.

These microchannels prevent the cell bodies from penetrating while at the same time allowing axon growth in one direction, as described above.

Photographs c and d are images by phase contrast combined with epifluorescence, of a polarized reconstructed neuronal network.

In order to visualize the individual axons on the cortical neurons, the cells were transduced with the M-cherry-Sindbis viral vector.

Photograph 1a represents the cortical neurons developing their axons in the second chamber and photograph 1d the striatal neurons seeded in the second chamber and receiving cortical neurons originating from the first chamber.

It can be noted that the striatal neurons are not contaminated by the virus, which is representative of an effective compartmentalization of the two culture chambers.

Scale bar: 50 µm.

Example 10: Corticostriatal Microfluidic Coculture with Increased Synaptic Maturation Photograph 3a of FIG. 15 represents striatal neurons, after culturing for three days in the second chamber of a device according to the invention, and cortical neurons seeded in the first chamber.

Cortical and striatal neurons are removed, by microdissection, from Swiss mouse embryos, the age of which was 14 days of gestation. All the dissection steps are carried out in PBS buffer supplemented with 0.1% of glucose. The microdissected structures are digested by incubation in a solution of trypsin-EDTA and dissociated mechanically with a pasteur pipette. After several rinses, the single-cell suspensions are counted. The cortical neurons are resuspended at $40 \times 10^6$ cells/ml in DMEM culture medium, the striatal neurons being resuspended at $15\text{-}20 \times 10^6$ cells/mi. The cortical and striatal neurons are then seeded into their respective culture chamber, the cortical neurons on the wide side of the microchannels. The culture reservoirs are then filled with culture media composed of DMEM containing glutamax, penicillin and streptomycin and neuronal supplements B27 and N2. The seeded microfluidic devices are then placed in an incubator at 37° C. The culture medium is renewed every 3 days.

After ten days of coculture, the neurons were labeled at the level of tubulin (green) and MAP 2 (red) and stained with DAPI (blue).

The cortical neurons sent their axons through the microchannels, exited from the microchannels and extended through the second culture chamber, where they are connected to the striatal neurons.

Photographs 3b and 3c represent a MAP E (blue)—tubulin (green) synaptic staining of a corticostriatal network and a pre- or post-synaptic (Vglut-1, synaptophysin or PSD95, red) labeling of (b) cortical neurons, or
(c) striatal neurons, and
(d) striatal neurons, in contact with the cortical fibers.

It can be noted, on photograph 3b, that the cortical neurons exhibit small and dispersed clusters of synaptophysin and of Vglut-1 on their axons, attesting to a partial maturation of the presynaptic terminals. Photograph 3c represents striatal neurons cultured separately, which exhibit scattered clusters of synaptophysin and PSD95, signaling an intermediate state of differentiation of the striatal neurons.

As expected, the striatal neurons cultured separately did not express Vglut-1.

Photograph 3d shows that the connections developed by the contact between the cortical fibers and the striatal dendrites result in increased labeling with grouping together of these three synaptic markers.

An increase in the staining and in the formation of clusters of synaptophysin, Vglut-1 and PSD95 can be noted, more particularly where the cortical axons and the striatal axons appear to be in contact with one another, attesting to a relocalization of the synaptic proteins at the corticostriatal contacts.

Photograph 3e represents, on an enlarged scale, a synaptic marker (red) toward the striatable dendrites (blue).

Scale bar for photograph 3a: 50 µm and for photographs 3b to 3e: 10 µm.

Example 11: Reconstitution of a Cortico-Hippocampal Network in a Microfluidic Device According to the Invention This experiment was carried out with the device D2.

Photograph a, in phase contrast, of FIG. 16 represents a device seeded with cortices alone, and photograph b, in phase contrast also, represents a device seeded with cortices in the left-hand chamber, extending onto hippocampal neurons. Photographs c, d and e correspond to immunofluorescent labelings.

Photograph c represents cortex axons seeded alone, photograph d cortex axons extending onto a hippocampal neuron. Photographs e and f represent a bundle of cortical axons (α-tubulin in green) demonstrating synaptic sprouting (grouping together of synaptophysin in red) in proximity to the dendrite (microtubule associated protein MAP2 in blue) of the hippocampal neuron.

Photograph f represents a cortex-dentate gyrus network, with a bundle of cortical fibers (tubulin, in green) contacting dentate gyrus neurons (Prox-1, red). Image g is similar, with labeling of the formation of cortico-hippocampal synapses (α-synaptophysin, red) along dendrites of dentate gyrus neurons (MAP2, blue). Magnification X400(a), X630(b). Scale bars 20 µm.

Example 12: Translocation of Cortical Pre-Synaptic Proteins on Contact with the Dendrites of Hippocampal Neurons Photograph a of FIG. 17 corresponds to synaptophysin (red) and axonal tubulin (green) labeling of cortical neurons seeded alone.

This experiment was carried out with the device D2.

Cortical neurons are taken, by microdissection, from Swiss mouse embryos, the age of which is 14 days of gestation. The hippocampal neurons are taken from mouse embryos, the age of which is 16 to 19 days. All the dissection steps are carried out in GBSS buffer supplemented with 0.1% of glucose. The microdissected structures are digested by incubation in a solution of papain-EDTA and dissociated mechanically with a pasteur pipette. After several rinses, the single-cell suspensions are counted. The cortical neurons are resuspended at 40×10⁶ cells/ml in DMEM culture medium, the hippocampal neurons being suspended at 15×10⁶ cells/ml. The cortical and hippocampal neurons are then seeded into their respective culture chamber, the cortical neurons on the wide side of the microchannels. The culture reservoirs are then filled with culture media composed of DMEM containing glutamax, penicillin and streptomycin and neuronal supplements B27 and N2. The seeded microfluidic devices are then placed in an incubator at 37° C. The culture medium is renewed every 3 days.

Photograph (b): hippocampal neurons seeded alone, without cortical afference: labeling of dendrites (MAP2, blue), of axons (tubulin, green) and of synaptophysin (red).

Images (c, d): bundles of cortical fibers (green) and synaptophysin of the hippocampus (MAP2, blue).

Intense labeling of the presynaptic proteins along the dendrites of the hippocampal neurons (synaptophysin, red) can be noted.

Image (e): magnification of a hippocampal dendrite. It can be noted that the synaptophysin is at the points of junction between the cortical fibers (tubulin in green) and the dendrite of the hippocampal neuron (MAP2 in blue). (a, b, c, d) scale bars 25 of scale 10 μm.

Example 13

FIG. 18 represents microfluidic chambers separated by asymmetrical microchannels.

This experiment was carried out with the device D3.

The cortical neurons are seeded on the left and the striatal neurons on the right. After seven days in vitro, the cortical axons establish connections with the striatal neurons (β3-tubulin in green, striatal neurons in red (MAP2)).

Depolarization with KCl triggers phosphorylation of the striatal erk kinase (in red), a process dependent on glutamate-mediated neurotransmission (as evaluated with inhibition with MK801).

Example 14: Evaluation of the Axon-Protecting Effect of Pharmacological Molecules of Therapeutic Interest Cerebellar neurons are seeded into microfluidic devices according to the invention and treated with an apoptosis inducer (1 μM staurosporin, STS) at the somatic level. This induces axonal degeneration in the distal chamber (Phi). Apoptosis-blocking compounds (zVAD) or proteases of calpain type (Cal-Inh) are applied specifically to the axons (and not to the somas). The "axon-protecting" effect is quantified on the graph on the right in FIG. 19.

Devices D1 are used.

Neurons (in this case from the cerebellum) are seeded and their axons pass through the asymmetrical microchannels so as to reach the second chamber (or the 3rd if the device has three compartments).

A stress (in this case staurosporin, which is a pro-apoptotic agent) is applied to the soma of the neurons. It induces axon degeneration in 24 h. The concomitant application, to the axon, of an apoptosis inhibitor (zVAD, or calpains (Cal-Inh)) prevents this degeneration. The effect of "axon-protecting" molecules can thus be evaluated.

FIG. 19 illustrates the start of axonal degeneration induced by the application of a pro-apoptotic stress applied to the somato-dendritic compartment of neurons. This causes the propagation of a destructive signal in the axon, which then degenerates early, before the cell soma. The application of apoptosis-blocking molecules (zVAD) or calpains (iCal), or of NAD, delays this axonal degeneration.

Example 15: Three-Chamber Device for the Localized Application of Molecules of Interest on a Portion of Axon The microfluidic device represented in image 4a of FIG. 20 is similar to that described previously with reference to FIGS. 1C to 1H and comprises three chambers. It is device D4. This makes it possible to apply molecules of interest on the central portion of the axons, for example a detergent (Triton X100, 0.1%), applied for 1 min. This causes an immediate section of the central portion of the axons, as illustrated by photograph 4b. In this example, although the cortical axons sectioned in their central portion are still intact after one hour of section, they degenerate after 4 h. This constitutes a model of Wallerian degeneration (degeneration of the distal portion of axons). The potential of compounds which protect against this effect can be evaluated by applying them specifically in one or more of the chambers of the device. Graph 4 of FIG. 20 quantifies the axon-protecting effect of NAD.

Example 16: Modeling of a Phenomenon of Synaptic Degeneration on a Corticostriatal Network, and Evaluation of Molecules of Interest Against Synaptic Degeneration. NAD+ Delays Deconnection Photographs a and b of FIG. 21 represent cortical, central and striatal chambers of reconstructed corticostriatal networks in three-chamber microfluidic devices.

The neurons were labeled on MAP2 (blue), β3-tubulin (green) and Vglut-1 (red).

Photograph a represents cortical neurons which have sent axons through the microchannels and the central chamber so as to reach and connect with striatal neurons.

Photograph b shows that, one hour after axotomy, there are no longer any axons present in the central chamber, but that the axons inside the microchannels and inside the prostriatal chamber have remained intact.

Photograph c is representative of cortical-presynaptic structures (Vglut1, red) attached to striatable dendrites (MAP2, blue) after 1, 2, 4 and 6 hours of axotomy or controlled culture or culture pretreated with NAD.

It is possible to note the decrease in Vglut-1 staining after such a short period of time and once after axotomy.

Photograph d illustrates the quantification of a presynaptic cortical structure attached to MAP2-positive striatal dendrites after cortical axotomy.

Scale on photographs 5a and b: 50 μm and photograph 5c: 5 μm.

This experiment was carried out with device D4. The experiment, carried out on a corticostriatal network, makes it possible to illustrate that it is possible to objectivize a phenomenon of synaptic degeneration after application of a stress at the cortical level (in this case axotomy) (disappearance of Vglu-1 labeling which is specific for cortical presynaptic structures). Example 15 shows that it is possible to objectivize a phenomenon of axonal degeneration. The experiment of example 16 also shows that it is possible to evaluate the role of synapse-protecting/stabilizing molecules after triggering of a remote stress. FIGS. 20 and 21 illustrate the consequences of the axotomy of cortical axons of a corticostriatal network. This axotomy causes the propagation of a signal resulting in rapid degeneration of the presynaptic compartment (FIG. 21) of the corticostriatal junction, and then in degeneration of the cortical axons (FIG. 20). Addition of the NAD molecule to the striatal compartment at the time of the axotomy delays presynaptic degeneration, and the degeneration of the transected cortical axons.

Example 18: Reconstitution of a Network of Three Types of Neurons in a Trichamber Device with a System of Perpendicularly Oriented Interconnections A device similar to that previously described with reference to FIG. 22 is used in this example.

The device D5, represented in FIGS. 22 and 23, composed of three culture chambers (ABC) separated by asymmetrical microchannels (lengths ranging between 500 and 100 µm between A and B, and 500 µm between B and C), is used.

The particularity of this device is that the chambers (macrochannels) A and B are perpendicular. The neurons (in this case from the cortex) seeded into chamber A project their axons into chamber B and continue straight on.

They are therefore oriented perpendicularly to the microchannels connecting chambers B and C. This avoids them passing right through chamber B so as to join up with chamber C. Cortical neurons are removed by microdissection from Swiss mouse embryos, the age being 14 days after gestation. The CA neurons are removed from 16-day-old mouse embryos, and the DG neurons are removed from young newborn mice of which the age is 5 days post-natal. All the dissection steps are carried out in GBSS buffer supplemented with 0.1% of glucose. The microdissected structures are digested by incubation in a solution of papain-EDTA and dissociated mechanically with a pasteur pipette. After several rinses, the single-cell suspensions are counted. The cortical neurons are resuspended at $40 \times 10^6$ cells/ml in DMEM culture medium, the hippocampal neurons being suspended at $15 \times 10^6$ cells/ml. The cortical and CA or DG neurons are then seeded into their respective culture chamber, the cortical neurons on the wide side of the diodes. The culture reservoirs are then filled with culture medium composed of DMEM containing glutamax, penicillin and streptomycin and neuronal supplements B27 and N2. The seeded microfluidic devices are then placed in an incubator at 37° C. The culture medium is renewed every 3 days.

The image of FIG. 23 represents cortical neurons seeded into the upper proximal chamber (in blue). The cortical axons pass through the microchannels and join up with the second chamber (in green). No target neuron is introduced into the other chambers. The rectilinear projections of the cortical axons can be noted on image b. Dentate gyrus DG neurons (the nuclei of which are labeled in red) are introduced into the intermediate chamber (in green on image f). It can be noted that the cortical axons in green converge toward the DG neurons. The projections of the DG neurons toward the distal chamber (in red on (f)) can also be noted.

Image (c) represents a three-neuron network reconstituted on the same principle as for images (a) and (b). The cortical neurons are seeded into the upper proximal chamber (not visible on this image). The cortical axons which leave the microchannels contact the DG neurons in the second chamber, boxed top left and in zoom on image (d). The DG neurons send their axons into the 3rd chamber and contact the hippocampal neurons, boxed bottom middle and visible on image (e).

Scale bars 250 µm, except for image (f), which is 5 mm.

Example 19: Detection of Proteins in Axonal Extracts of Cortical Neurons Developed in a Microfluidic Chamber Scheme a of FIG. 24 illustrates a microfluidic device comprising three interconnected chambers. The neurons are seeded into the two lateral chambers and their respective axons reach the central chamber. The microfluidic chambers are fluidically isolated by hydrostatic pressure. Just before axonal lysis, the cell culture chambers containing the soma of the neurons are filled with agarose gel. This ensures permanent isolation of the somatic compartment. The cell lysis buffer circulates in the central compartment and allows specific recovery of the axonal material without somatic contamination.

Photograph b illustrates colloidal gold staining of a single somatic and axonal extract.

The device used is device D6.

Mouse cortex neurons are seeded into the two exterior channels and the axons of these neurons join up with the central chamber. This makes it possible to increase the amount of axonal material in the central chamber. At the end of the cell culture period, a lysis buffer is perfused into the compartment (axonal or somatic) that it is desired to specifically sample. This sample can then be subjected to subsequent analyses, in this case acrylamide gel electrophoresis and visualization by the Western blotting technique.

Prior to the lysis buffer perfusion step, a gel (for example in this case: low-melting-point agarose) can be introduced into the compartments that it is not desired to sample. This makes it possible to "set" these compartments and ensures a perfect fluidic isolation when the lysis buffer is perfused into the compartment to be sampled.

Photograph c illustrates a Western blot typical both of the axonal and somatic compartments for MAP2 (dendritic) and beta-3-tubulin (axonal) and actin.

Example 20

In this example, a microfluidic device for neuron culture having three chambers, as represented in FIGS. 1C to 1H, is used.

The microchannels are used to direct axon growth and compartmentalize the cultures. These three-compartment neuronal circuits were fabricated using photolithography methods, as previously described. The architecture of these microfluidic circuits comprises a somatic chamber (macrochannel) and an axonal chamber (macrochannel), each 1 mm long, and a central chamber 100 µm long. The chambers are connected to one another via a series of parallel microchannels 10 µm wide, 3 µm thick and 450 µm long, and spaced out 20 µm from one another, as in FIGS. 1C to 1H. The thickness of the somatic, central and axonal compartments is 55 µm. In order to fabricate masters having channels of two different heights, two layers of photosensitive resin are used. The silicon masters are first heated at 150° C. and activated by plasma treatment for 30 s. The first layer of photosensitive resin SU8-2002 (Microchem, Newton, USA) is spin-coated onto the silicon plate at 2000 rpm and then a re-curing is performed at 65° C. for 2 min and a re-curing is performed at 95° C. for 4 min. The resin is then exposed to UV light through an optical mask in which the microchannels are drawn. After further re-curing, the microchannels 2-3 µm thick are developed with the SU8 developer (Microchem). A film of SY355 resin (Elga Europe, Milan, Italy), 55 µm thick, is then laminated at 80° C. onto the master already having the microchannels. A second mask having the geometry of the three compartments is then aligned on the pre-existing microchannels and exposed to UV rays. The whole is then cured at 120° C. for 5 min and the second layer is developed in the BMR developer (Elga Europe). The whole is finally rinsed with isopropanol. A master consisting of compartments and of microchannels in relief made of resin, which lie on a silicon wafer, is thus obtained. Each master has four identical microfluidic circuits comprising chambers and microchannels. An elastomer, namely polydimethylsiloxane (PDMS), is subsequently molded using these masters. The noncrosslinked PDMS (Dow Corning, Midland, Mich.) is poured onto the masters and then crosslinked in an oven at 70° C. for three hours. A layer, 4-5 mm thick, of shaped PDMS is obtained after curing. Holes of 4 mm are subsequently pierced in this layer of PDMS, using biopsy punches, and constitute culture medium reservoirs. The holes thus formed are slightly wider than the reservoirs molded in the PDMS using the master; they completely encompass them and are directly connected to the various compartments of the circuit. Each PDMS molding is subsequently irreversibly attached to a glass coverslip (Menzel Glass, Braunschweig, Germany) via activation of the surfaces (molded face of the PDMS and one face of the glass coverslip) with an air plasma generator (Diener Electronic, Nagold, Germany) followed by manually bringing the two activated surfaces into contact. The circuits thus formed are sterilized by exposure to UV radiation and treated overnight with a solution of poly-D-lysine (Sigma, Saint Louis, USA) at 10 µg/ml so that the internal surfaces of the circuit remain hydrophilic.

Neuron Cultures and Treatments

The cortices of 14-day mouse embryos are dissected and dissociated as has already been described elsewhere, for example Eur J Neurosci 2001 June; 13(11): 2037-46 William S et al. The neurons are seeded into the somatic chamber (also called compartment) of the circuits at a density of $10^5$ cells/cm$^2$. In this manner, about $4 \times 10^4$ neurons are seeded into the somatic chamber. The culture medium consists of DMEM containing 4.5 g/l D-glucose and pyruvate (Invitrogen, Carlsbad, USA), supplemented with 10% of FCS (fetal calf serum; PAA Laboratories, Pasching, Germany) and with 2% of B27 (Invitrogen). The medium is replaced every three days until the beginning of the experiment, and the cultures are conserved in an incubator at 37° C. and 5% $CO_2$. The experiments are carried out after 7 to 8 days of culture in vitro. The calpain inhibitor N-acetyl-Leu-Leu-Nle-CHO (ALLN; Calbiochem), the general caspase inhibitor Z—V-A-D-fluoromethyl ketone (z-VAD; R1D Systems, Minneapolis, USA) and β-nicotinamide adenine dinucleotide hydrate (βNAD; Sigma) are introduced into the culture medium at the beginning of the experiments.

Axotomy Procedure

In order to carry out the axotomy, a flow of 15 µl of medium containing 0.1% of saponin is produced for 2 minutes in the central chamber. In order to avoid the flow of detergent entering the microchannels, an overpressure is maintained in the somatic and axonal chambers throughout the experiment. After 2 minutes of flow, the medium containing the saponin is removed and the central macrochannel is rinsed with culture medium for 5 min. Fresh medium is then added to this channel.

Flow and Diffusion Experiments

A series of qualitative experiments for measuring flow and diffusion were carried out in order to verify (i) that the axotomy is localized in the central chamber and (ii) that the long-term treatments remain confined in the compartments in which they are targeted. In order to simulate the axotomy procedure, an experiment was carried out by producing a flow of fluorescent microspheres 1 µm in diameter (Invitrogen) in suspension in a mixture of PBS and saponin, and by following the flow of these beads by video microscopy. Furthermore, anti-rabbit immunoglobulin G antibodies conjugated to an Alexa Fluor 555 (IgG; 1:100, Invitrogen) were used as a diffusion tracer in order to simulate the effect of the diffusion of particles both during the axotomy and during the long-term treatments. The relationship between the fluorescence intensity in the circuit and the concentration of the label was established by capturing images of the microfluidic compartments pre-filled with solutions containing the label at known concentrations. A linear relationship ($R^2 > 0.99$) was demonstrated between the intensity of the fluorescent signal and the concentration of the tracer. In each experiment, three circuits were analyzed and, in each of these circuits, images of three different regions of each compartment were taken at various times in order to quantify the diffusion of the fluorescent label (i) starting from the central compartment and moving to the somatic compartment for the experiments mimicking axotomy, (ii) from the axonal compartment and moving to the central and then somatic compartments for the experiments mimicking the long-term treatments. The nonspecific signal was obtained by performing an acquisition with the DAPI filter and was subtracted from the Alexa Fluor 555 signal in order to eliminate the variation in intensity of the signal due to local variations in illumination intensity. Axotomy was mimicked by adding a 100% solution of the label to the detergent solution and placing the same volumes of solutions in the reservoirs as for a real axotomy. The images of FIG. 25 were taken, respectively, 2, 5 and 10 min after the addition of the detergent solution containing the label to the reservoir of the central compartment. The experiments mimicking the diffusion of molecules in the long term were carried out by introducing the solution containing the label into the axonal chamber and maintaining the equilibrium of the pressures in the circuit by placing identical volumes of liquid in all the reservoirs. The images were taken 1, 2, 4 and 8 hours after the addition of the label to the axonal chamber.

Immunocytochemistry

After a given culture time (optionally according to the moment at which the axotomy experiment is carried out), the neuron cultures are fixed with a 4% paraformaldehyde solution (Sigma) so as to undergo analysis by immunocytochemistry. The circuits are labeled by immunofluorescence with an anti-MAP2 antibody (rabbit IgG, 1:3000; Chemicon, Temecula, USA), and an anti-β-III-tubulin monoclonal antibody (mouse IgG, 1:3000; Sigma) for labeling the cytoskeletal proteins. The circuits are fluorescently labeled with Hoechst 33342 (1:25000; Sigma) for labeling the nucleus. In a separate experiment, the circuits were also labeled by immunofluorescence with an anti-glial fibrillary acidic protein antibody (GFAP, rabbit IgG, 1:5000; DakoCytomation, Glostrup, Denmark) which makes it possible to label the astrocytes. A part of the cultures was subjected to fixing and extraction. This procedure makes it possible to eliminate the tubulin free in the cytoplasm while at the same time fixing the microtubules. These cultures were labeled by immunofluorescence with an anti-a-tubulin monoclonal antibody conjugated to the fluorophore FITC (Sigma) and labeled with phalloidin linked to an Alexa Fluor 555 (Invitrogen) so as to reveal the microtubules and the actin cytoskeleton, respectively. The images were acquired using an inverted epifluorescence microscope (Zeiss, Goettingen, Germany) equipped with a CoolSnap HQ2 camera (Roper Scientific, Ottobrunn, Germany) and using the micro-manager acquisition software (http://www.micro-manager.org).

Quantification

The axonal degeneration is estimated by comparing the type of tubulin labeling of fragmented axons or of intact axons. Good survival, in culture, of the cortical neurons is dependent on the initial seeding density, which must be high. Consequently, a large number of cortical axons invade the central and distal chambers. Moreover, since the cortical axons have many branches, the immunohistochemical analysis of the axonal tubulin in the axonal chambers is therefore complex, and the axons are difficult to individualize. The proportion of axon entering the central chamber and emerging in the distal axonal chamber was estimated by calculating a ratio of intensity of overall fluorescence of the b3-tubulin labeling of identical surface areas captured in the central chamber and the distal axonal chamber. In order to measure the axonal fragmentation index, an automated image analysis method can be used. The images of viable or fragmented axons, labeled for 3-tubulin, are captured by epifluorescence microscopy. The fragmented axons exhibit a punctate and discrete tubulin labeling; on the other hand, the intact axons exhibit a linear labeling. Using a macro-control developed under the Image J software, and using sequentially an Otsu segmentation algorithm (see IEEE Trans Systems, Man and Cyber Metics 1979; 9:92-69) and a particulate analysis algorithm, the axonal segments exhibiting a circularity index>=0.9 are considered to be fragmented axon segments. For each image, the total surface area of this type of labeling (circularity>=0.9) is determined and related to the total surface area of each tubulin labeling (independently of the topology of the labeling). This ratio is called the "fragmentation index" and is an indicator of the mean state of fragmentation of the axons studied. FIG. 30 shows the relationship between the fragmentation index and the % of fragmented axons, 0.005, 0.083 and 0.157 corresponding, respectively, to <5%, 50% and >95% of fragmented axons. The survival of the neuronal somas is evaluated i) by analysis of the nuclear chromatin condensation revealed by DAPI labeling and ii) by analysis of the dendritic morphology after MAP2 labeling. At least five images per condition were analyzed (each condition being triplicated), the experiments having been carried out at least three times independently.

Statistical Analysis

The data are expressed in the form of means+/−standard deviation from the mean (sem). N represents the number of individual circuits. The statistical analysis is carried out by means of a one-way analysis of variance (ANOVA), followed by a Tukey test.

Results

Control of the Fluid Flows in the Axotomy Compartment

In order to characterize the flow of fluids in the central chamber of the device, experiments relating to flow of a suspension of fluorescent beads in a dilution of detergent can be carried out. In order to obtain a control flow in a compartment, a pressure gradient is produced by placing different volumes of liquid in the reservoirs connected to the corresponding chamber. Thus, it is possible to follow, by video microscopy, the flow of the suspension of beads in the central channel when the inlet and outlet reservoirs are filled with 15 and 0 μl, respectively, while the two connected chambers are pressurized with 40 μl of PBS in each of their reservoirs (all the reservoirs having the same dimensions). The images acquired during the first 180 seconds show that the detergent solution does not enter the microchannels which adjoin the central chamber. In the bottom part (also called macrochannel) of the central channel, the beads are constrained in the central part of the chamber, thus showing the existence of a flow from the overpressured chambers to the central chamber; there is therefore focusing of the suspension of detergent in the central channel (FIG. 25*a*). Using the same fluidic conditions, the opposite experiment, consisting of filling the two distal chambers with a suspension of beads, while a flow of PBS is generated in the central chamber, shows that, under these conditions, a flow from the distal chambers to the central chamber can be objectivized through the movement of beads in the microchannels (FIGS. 25*b* and 25*c*). Moreover, in order to determine more precisely the parameters of the gradients generated in this flow configuration, and to simulate an axotomy experiment, a dilution of fluorescent immunoglobulin was used as tracer. No diffusion of the fluorescent Ig could be detected from the central chamber into the microchannels. In the bottom part of the central chamber, after 2 minutes of flow, dispersion of the tracer in the chamber (along the cross section of the chamber) becomes established according to a Gaussian distribution, the peak of which is at the center of the chamber, so as to reach a value of zero at the edges. This shows that the fluorescent immunoglobulin is well-confined in the central channel by the flow originating from the two overpressurized distal chambers (FIG. 25*d* and table 1 hereinafter). The reverse experiment was carried out by adding the tracer to the two distal chambers and shows the flow from the distal chambers to the central chamber.

TABLE 1

Experiment relating to diffusion of a tracer during axotomy. The concentration of tracer is linearly related to the fluorescent signal intensity ($R^2 > 0.99$). The values are given as % of the maximum concentration and represent the mean of three independent experiments.

|  | 2 min | 5 min | 10 min |
| --- | --- | --- | --- |
| Somatic compartment | 0.02 ± 0.29 | 0.18 ± 0.30 | 0.29 ± 0.31 |
| Central compartment | 68.4 ± 9.8 | 58.1 ± 3.9 | 44.9 ± 5.8 |

Additional experiments were carried out in order to study the diffusion of tracers from one chamber to the other during a long-term compartmentalization. Identical volumes of liquid were introduced into all the reservoirs (no flow generated) and the fluorescent tracer was added to one of the distal chambers. 2 hours after the addition of the tracer, approximately 15% of the tracer is found in the central chamber, and nothing in the opposite distal chamber, thus showing that the central chamber serves as a "buffer" for providing perfect compartmentalization of the two distal chambers, the central chamber playing, in this configuration, the role of a "syphon". The values are indicated in table 2.

TABLE 2

Long-term tracer diffusion experiment. The concentration of tracer is linearly related to the fluorescent signal intensity ($R^2 > 0.99$). The values are given as % of the maximum concentration and represent the mean of three independent experiments.

|  | 0 h | 1 h | 2 h | 4 h | 8 h |
| --- | --- | --- | --- | --- | --- |
| Axonal compartment | 83.2 ± 7.91 | 72.8 ± 0.52 | 66.7 ± 0.55 | 76.1 ± 4.79 | 69.4 ± 10.7 |
| Central compartment | 1.41 ± 1.36 | 4.23 ± 4.25 | 13.3 ± 0.70 | 13.5 ± 0.11 | 13.1 ± 0.60 |
| Somatic compartment | 0.26 ± 0.13 | 0.34 ± 0.13 | 0.32 ± 0.02 | 0.37 ± 0.15 | 0.26 ± 0.00 |

As a whole, these experiments which are the subject of example 20 show i) that it is possible to carry out a controlled and confined flow in the central chamber without any diffusion from this chamber to the two adjacent distal chambers; ii) that the long-term diffusion of molecules introduced into a distal chamber toward the second distal chamber is completely abolished by the presence of a central chamber, thereby making it possible to be sure that there is perfect fluidic isolation from an axonal chamber to a somatic chamber (or vice-versa).

Differentiation of Cortex Neurons

Neurons derived from the cortex of embryonic mice are seeded at relatively high density in the "somatic" chamber. The axons of approximately 3 to 5% (close to the microchannel zone) of the seeded neurons penetrate into the 167 microchannels which join up with the central chamber. Phenotyping of the seeded cells after 8 days of culture shows that the culture is composed of to 90% of neurons (MAP2 positive), 5 to 8% of astrocytes (GFAP-positive) and of microglial (1%) and fibroblast (1%) cells. Under the seeding conditions carried out, approximately 10 to 15 axons enter per microchannel. The analysis by immunocytochemistry of the axonal tubulin shows that 38.8%+/−3.4% (n=11) of the axons having invaded the central chamber (100 μm in width) effectively join up with the second distal chamber after 8 days of culture (the proportion being approximately 60% when the width of the central chamber is 50 μm). After 10 days of culture, the mean length of the cortical axons having passed through the central chamber and joined up with the second distal chamber is 1.5 to 2 mm (FIG. 26). The axons are confined in bundles in the microchannels, and have a tendency to unbundle on leaving the microchannels (FIG. 26a). The central compartment of the device can therefore be used to locally apply a treatment, on the median portion of the axons.

Axotomy of Cortex Neurons Induces Growth Cone Coalescence and a "Wallerian Degeneration" Phenomenon.

The axotomy of the cortical neurons is carried out by creating a flow (under the conditions described in paragraph 1) for 2 minutes in the central compartment, of culture medium containing 0.1% of saponin. The flow of detergent causes an immediate destruction of the axon segments contained in the central compartment (FIG. 26b), thus causing a transsection located approximately 500 to 600 μm from the neuronal soma. The axotomy causes a progressive degeneration of the distal portion of the axons, resulting in the early formation of distension of the axonal segments, followed by fragmentation of the microtubule network (FIG. 27a). The axonal fragmentation was quantified at various times post-axotomy, and indicates that the fragmentation index differs significantly from the untreated controls after 4 h (the "sham" controls underwent the same flow conditions (omitting the saponin) as the axons treated with saponin). The fragmentation increases significantly between all the analysis times, and reaches a plateau, corresponding to the total destruction of all the axons, after 8 h (FIG. 27b).

The presence of growth cones at the distal end of the cortical axons is indicative of correct axonal growth, the neuron seeking its target. The growth cones, which are low in tubulin, exhibit a characteristic dynamic morphology where the actin filaments form filopodia and lamellipodia (see J. Neurobiol. 2004; 58(1): 92-102). Although, in the control neurons, a very large number of growth cones can be objectivized by actin labeling, 1 hour after axotomy, while the microtubule network is still intact, the transected axons exhibit growth cones which have collapsed at their tip (FIG. 28a). This indicates that a destructive signal is propagated to the distal end of the axons rapidly after axotomy.

In vivo, the axotomy of peripheral neurons has been shown as being an asynchronous phenomenon. At a given time, the transected axons exhibit morphologies ranging from the intact structure to complete fragmentation, anterograde propagation of the degeneration having been suspected. In our experimental model, in the early phases of axotomy (<4 h), intact, distended or fragmented axons can be observed, suggesting the triggering of a slight asynchronous phenomenon (FIG. 28b). Analysis of the unique segments of transected axons after 6 h shows that the same axon can exhibit signs of fragmentation in the proximal regions (close to microchannels), of distension in the median part, and of intact segments in their completely distal part. This suggests a phenomenon of anterograde propagation of a wave of degeneration toward the tip of the axon (FIG. 28c).

Distal Degeneration is Slowed Down by bNAD but not by Caspase Inhibition or Calpain Inhibition The early activation of calpains has been described after axotomy of peripheral nervous system neurons. On the other hand, although they are activated in the somas of axotomized neurons, the inhibition of caspases does not prevent degeneration of the cut neurons. The involvement of calpains and caspases in axonal degeneration induced by axotomy of cortical neurons can be evaluated as follows. The application, to the distal segments of axons, at the time of axotomy, of 50 μM of ALLN, which is a calpain inhibitor, or of 50 μM of z-VAD, which is a general caspase inhibitor, does not delay the occurrence of axon fragmentation, nor modify the parameters thereof (FIG. 29). An absence of protective effect is also observed when these molecules are applied 24 h before axotomy (not shown). On the other hand, when the neurons are pretreated, 24 h before axotomy, with 5 mM of the bNAD molecule, the signs of axonal degeneration are delayed. Although all the control axons are fragmented, 8 h after axotomy, the cut axons do not exhibit any sign of degeneration. This protection disappears 24 hours after axotomy (FIG. 29).

FIG. 31 indicates the proportion of somatic deaths, obtained by dividing the number of cell bodies showing labeling with Hoechst dye by the total number of bodies. No significant change in somatic death was observed 24 hours after axotomy, with or without treatment, compared with the controls.

Example 20 above can be carried out with a system of interconnection with microchannels of optionally constant width.

A subject of the invention, according to another of its aspects, is thus also a method of axotomy using a microfluidic device comprising at least three chambers, for example as represented in FIG. 1B or 1C to 1H, with microchannels having an optionally constant width, in which a compound is injected into the central chamber so as to act on at least one axon extending into the microchannels, in order to carry out the axotomy. The distal chambers may be at overpressure relative to the distal chamber.

The invention is not limited to the examples described.

The expression "comprising one" should be understood to be synonymous with "comprising at least one".

The invention claimed is:

1. A device for cell culture comprising:
a support defining a first microfluidic chamber seeded with a first cell culture, and at least one second microfluidic chamber, and
a fluidic interconnection system connecting the first and the at least one second microfluidic chambers, wherein:
the fluidic interconnection system is arranged for directing cell connection between the first microfluidic chamber and the at least one second microfluidic chamber, and comprises at least one microchannel, wherein a width of the at least one microchannel monotonically decreases from the first microfluidic chamber to the at least one second microfluidic chamber, the at least one microchannel comprises at least one portion having a width that decreases from the first microfluidic chamber to the at least one second microfluidic chamber, and configured to promote progression of at least one first type of cell extension compared with at least one second type of cell extension, said first and second types of cell extension differing either by virtue of the microfluidic chamber from which they originate, or by virtue of the cell type of which they are the extension, and each one of the first microfluidic chamber and the at least one second microfluidic chamber comprises a macrochannel, an end of each macrochannel connected to a reservoir, wherein the at least one microchannel connects the macrochannel of the first microfluidic chamber to the macrochannel of the at least one second microfluidic chamber.

2. The device as claimed in claim 1, further comprising a third microfluidic chamber communicating with the fluidic interconnection system.

3. The device as claimed in claim 1, wherein the at least one microchannel comprises a plurality of microchannels.

4. The device as claimed in claim 1, wherein the at least one microchannel has at least one portion having a trapezoidal shape when observed from above.

5. The device as claimed in claim 1, wherein the at least one microchannel has a non rectilinear axis.

6. The device as claimed in claim 1, wherein a surface of at least one portion of the fluidic interconnection system has been chemically or biochemically treated so as to have an affinity for at least one type of cell or one type of cell behavior.

7. The device as claimed in claim 1, wherein the at least one microchannel has a thickness that is less than those of the first and the at least one second microfluidic chambers.

8. The device as claimed in claim 1, comprising at least one single-cell microfluidic chamber, proportioned so as to contain only a soma of a single cell, this single-cell microfluidic chamber communicating with the interconnection system and with one of the first and the at least one second microfluidic chambers.

9. The device as claimed in claim 1, wherein the width of the at least one portion of the at least one microchannel decreases linearly.

10. The device as claimed in claim 1, wherein the at least one microchannel consists of a trapezoidal shape when viewed from above.

11. The device as claimed in claim 1, wherein the at least one microchannel comprises at least one portion that has a constant width and at least one portion that has a trapezoidal shape when viewed from above.

12. The device as claimed in claim 1, wherein the at least one microchannel comprises successively at least one portion having a constant width, at least one portion having a trapezoidal shape when viewed from above, and at least another portion having a constant width.

13. The device as claimed in claim 1, wherein the at least one microchannel has an asymmetrical shape, with a wider portion and a narrower portion, connected via an intermediate portion having a width which decreases linearly.

14. The device as claimed in claim 1, wherein the at least one microchannel comprises a bifurcation with at least two branches.

15. The device as claimed in claim 1, further comprising at least one microelectrode.

16. The device as claimed in claim 1, further comprising a network of microelectrodes.

17. The device as claimed in claim 1, wherein the device is configured to enable oriented reconstruction of neuronal networks, optionally involving various neuronal subtypes, and/or a combination of neurons and of non-neuronal cells, and/or various types of axonal and/or dendritic interactions between neurons.

18. The device as claimed in claim 1, wherein the at least one second microfluidic chamber is seeded with a second cell culture.

19. The device as claimed in claim 17, wherein the at least one second microfluidic chamber is seeded with a second cell culture.

* * * * *